(12) United States Patent
Olmarker et al.

(10) Patent No.: US 7,708,995 B2
(45) Date of Patent: *May 4, 2010

(54) USE OF TNF-ALPHA INHIBITORS FOR TREATING A NERVE DISORDER MEDIATED BY NUCLEUS PULPOSUS

(75) Inventors: Kjell Olmarker, Molndal (SE); Bjorn Rydevik, Gothenburg (SE)

(73) Assignee: Sciaticon AB, Molndal (SE)

(*) Notice: Subject to any disclaimer, the term of this patent is extended or adjusted under 35 U.S.C. 154(b) by 240 days.

This patent is subject to a terminal disclaimer.

(21) Appl. No.: 11/521,093

(22) Filed: Sep. 14, 2006

(65) Prior Publication Data

US 2007/0104711 A1    May 10, 2007

Related U.S. Application Data

(63) Continuation of application No. 10/225,237, filed on Aug. 22, 2002, now Pat. No. 7,115,557, which is a continuation-in-part of application No. 09/826,893, filed on Apr. 6, 2001, now abandoned, which is a continuation-in-part of application No. 09/743,852, filed as application No. PCT/SE99/01671 on Sep. 23, 1999, now Pat. No. 6,649,589.

(30) Foreign Application Priority Data

Sep. 25, 1998 (SE) ................... 9803276
Oct. 29, 1998 (SE) ................... 9803710

(51) Int. Cl.
*A61K 39/395* (2006.01)
*C07K 16/24* (2006.01)
*C07K 16/28* (2006.01)

(52) U.S. Cl. ............ 424/130.1; 424/133.1; 424/135.1; 424/141.1; 424/142.1; 424/145.1

(58) Field of Classification Search .............. None
See application file for complete search history.

(56) References Cited

U.S. PATENT DOCUMENTS

| | | | |
|---|---|---|---|
| 4,666,897 A | 5/1987 | Golub et al. | |
| 4,925,833 A | 5/1990 | McNamara et al. | |
| 5,304,633 A | 4/1994 | Tomita et al. | |
| 5,395,760 A | 3/1995 | Smith et al. | |
| 5,565,272 A | 10/1996 | Masui et al. | |
| 5,565,425 A | 10/1996 | Yamamoto et al. | |
| 5,574,022 A | 11/1996 | Roberts et al. | |
| 5,602,157 A | 2/1997 | Christensen, IV | |
| 5,605,690 A | 2/1997 | Jacobs et al. | |
| 5,650,396 A | 7/1997 | Carlino et al. | |
| 5,656,272 A | 8/1997 | Le et al. | |
| 5,672,347 A | 9/1997 | Aggarwal et al. | |
| 5,686,428 A | 11/1997 | Eriksson | |
| 5,698,195 A | 12/1997 | Le | |
| 5,703,092 A | 12/1997 | Xue et al. | |
| 5,756,482 A | 5/1998 | Roberts et al. | |
| 5,763,446 A | 6/1998 | Sadun et al. | |
| 5,795,967 A | 8/1998 | Aggarwal et al. | |
| 5,919,452 A | 7/1999 | Le | |
| 5,945,397 A | 8/1999 | Smith et al. | |
| 5,962,481 A | 10/1999 | Levin et al. | |
| 6,001,828 A | 12/1999 | Andrulis, Jr. et al. | |
| 6,015,557 A | 1/2000 | Tobinick et al. | |
| RE36,755 E | 6/2000 | Smith et al. | |
| 6,177,077 B1 | 1/2001 | Tobinick | |
| 6,180,355 B1 | 1/2001 | Alexander et al. | |
| 6,201,105 B1 | 3/2001 | Smith et al. | |
| 6,277,966 B2 | 8/2001 | Kayane et al. | |
| 6,277,969 B1 | 8/2001 | Le | |
| 6,284,471 B1 | 9/2001 | Le | |
| 6,319,910 B1 | 11/2001 | Amin et al. | |
| 6,379,666 B1 | 4/2002 | Tobinick | |
| 6,406,867 B1 | 6/2002 | Yu et al. | |
| 6,419,934 B1 | 7/2002 | Tobinick | |
| 6,419,944 B2 | 7/2002 | Tobinick | |
| 6,423,321 B2 | 7/2002 | Tobinick | |
| 6,428,787 B1 | 8/2002 | Tobinick | |
| 6,471,961 B1 | 10/2002 | Tobinick | |
| 6,537,549 B2 | 3/2003 | Tobinick | |
| 6,572,852 B2 | 6/2003 | Smith et al. | |
| 6,623,736 B2 | 9/2003 | Tobinick | |
| 6,635,250 B2 | 10/2003 | Olmarker et al. | |
| 6,649,589 B1 | 11/2003 | Olmarker et al. | |
| 6,790,444 B2 | 9/2004 | Le | |
| 6,835,823 B2 | 12/2004 | Le | |
| 6,896,904 B2 | 5/2005 | Spiro et al. | |
| 6,982,089 B2 | 1/2006 | Tobinick | |
| 6,991,791 B2 | 1/2006 | Le | |
| 7,070,775 B2 | 7/2006 | Le | |
| 7,101,674 B2 | 9/2006 | Le | |
| 7,115,557 B2 | 10/2006 | Olmarker | |
| 7,128,907 B2 | 10/2006 | Le | |
| 7,128,908 B2 | 10/2006 | Le | |
| 7,135,178 B2 | 11/2006 | Le | |
| 7,135,179 B2 | 11/2006 | Le | |
| 7,138,118 B2 | 11/2006 | Le | |
| 7,160,542 B2 | 1/2007 | Le | |
| 7,160,543 B2 | 1/2007 | Le | |

(Continued)

FOREIGN PATENT DOCUMENTS

DE          4 028 487          3/1992

(Continued)

OTHER PUBLICATIONS

U.S. Appl. No. 09/256,388, filed Feb. 24, 1999.

(Continued)

*Primary Examiner*—Christine J Saoud
*Assistant Examiner*—Jon M Lockard
(74) *Attorney, Agent, or Firm*—Fish & Richardson P.C.

(57) ABSTRACT

The present invention relates to a method and a pharmaceutical composition for treatment of nerve disorders comprising administration of a therapeutically effective dosage of at least two substances selected from the group consisting of TNF inhibitors, IL-1 inhibitors, IL-6 inhibitors, IL-8 inhibitors, FAS inhibitors, FAS ligand inhibitors, and IFN-gamma inhibitors. Preferably, at least one of the substances is a TNF inhibitor.

13 Claims, No Drawings

U.S. PATENT DOCUMENTS

| | | | |
|---|---|---|---|
| 7,160,995 | B2 | 1/2007 | Le |
| 7,166,284 | B2 | 1/2007 | Le |
| 7,169,386 | B1 | 1/2007 | Le |
| 7,169,388 | B2 | 1/2007 | Le |
| 7,179,466 | B2 | 2/2007 | Le |
| 7,179,893 | B2 | 2/2007 | Le |
| 7,192,584 | B2 | 3/2007 | Le |
| 7,204,985 | B2 | 4/2007 | Le |
| 7,214,376 | B2 | 5/2007 | Le |
| 7,214,658 | B2 | 5/2007 | Tobinick |
| 7,223,396 | B2 | 5/2007 | Le |
| 7,226,250 | B2 | 6/2007 | Gatton |
| 7,226,593 | B2 | 6/2007 | Le |
| 7,227,003 | B2 | 6/2007 | Le |
| 7,252,823 | B2 | 8/2007 | Le |
| 7,276,239 | B2 | 10/2007 | Le |
| 7,335,358 | B2 | 2/2008 | Le |
| 7,374,761 | B2 | 5/2008 | Le |
| 7,404,955 | B2 | 7/2008 | Le |
| 7,416,729 | B2 | 8/2008 | Le |
| 7,425,330 | B2 | 9/2008 | Le |
| 2001/0027175 | A1 | 10/2001 | Olmarker |
| 2001/0053764 | A1 | 12/2001 | Sims |
| 2001/0055594 | A1 | 12/2001 | Olmarker |
| 2002/0131954 | A1 | 9/2002 | Tobinick |
| 2002/0132307 | A1 | 9/2002 | Le |
| 2002/0141996 | A1 | 10/2002 | Le |
| 2002/0146419 | A1 | 10/2002 | Le |
| 2003/0007972 | A1 | 1/2003 | Tobinick |
| 2003/0113318 | A1 | 6/2003 | Tobinick |
| 2003/0133935 | A1 | 7/2003 | Le |
| 2003/0147891 | A1 | 8/2003 | Le |
| 2003/0176332 | A1 | 9/2003 | Olmarker |
| 2003/0180299 | A1 | 9/2003 | Le |
| 2003/0185826 | A1 | 10/2003 | Tobinick |
| 2003/0204066 | A1 | 10/2003 | Le |
| 2004/0115200 | A1 | 6/2004 | Le |
| 2004/0120977 | A1 | 6/2004 | Dodd |
| 2004/0126372 | A1 | 7/2004 | Banerjee et al. |
| 2004/0136990 | A1 | 7/2004 | Banerjee et al. |
| 2004/0229878 | A1 | 11/2004 | DiMauro et al. |
| 2005/0025765 | A1 | 2/2005 | DiMauro et al. |
| 2005/0074454 | A1 | 4/2005 | Le |
| 2005/0112091 | A1 | 5/2005 | DiMauro et al. |
| 2005/0209603 | A1 | 9/2005 | Zucherman et al. |
| 2005/0220971 | A1 | 10/2005 | Coburn |
| 2005/0249735 | A1 | 11/2005 | Le |
| 2005/0255104 | A1 | 11/2005 | Le |
| 2005/0260201 | A1 | 11/2005 | Le |
| 2006/0009385 | A1 | 1/2006 | Hoffman et al. |
| 2006/0018907 | A1 | 1/2006 | Le |
| 2006/0046960 | A1 | 3/2006 | McKay et al. |
| 2006/0046961 | A1 | 3/2006 | McKay et al. |
| 2006/0051381 | A1 | 3/2006 | Tobinick |
| 2006/0551381 | | 3/2006 | Tobinick |
| 2006/0246073 | A1 | 11/2006 | Knight |
| 2006/0247623 | A1 | 11/2006 | Anderson et al. |
| 2006/0253100 | A1 | 11/2006 | Burright et al. |
| 2007/0087031 | A1 | 4/2007 | Ashman et al. |
| 2007/0104711 | A1 | 5/2007 | Olmarker |
| 2007/0196373 | A1 | 8/2007 | Le |
| 2007/0196375 | A1 | 8/2007 | Tobinick |
| 2007/0237777 | A1 | 10/2007 | DiMauro et al. |
| 2007/0243228 | A1 | 10/2007 | McKay |
| 2007/0298040 | A1 | 12/2007 | Le |
| 2008/0019964 | A1 | 1/2008 | Olmarker |
| 2008/0025976 | A1 | 1/2008 | Le et al. |
| 2009/0022718 | A1 | 1/2009 | Le et al. |

FOREIGN PATENT DOCUMENTS

| | | |
|---|---|---|
| DE | 4 219 626 | 12/1993 |
| EP | 0418014 | 12/1995 |
| EP | 1115405 | 5/2007 |
| JP | 07-145196 | 6/1995 |
| JP | 07-274970 | 10/1995 |
| JP | 07-309771 | 11/1995 |
| JP | 08-040925 | 2/1996 |
| JP | 08-073499 | 3/1996 |
| JP | 08-143468 | 6/1996 |
| JP | 09-165342 | 6/1997 |
| SE | 9803276-6 | 9/1998 |
| SE | 9803710-4 | 10/1998 |
| SE | 9803710-4 | 3/2000 |
| SE | 0200667-4 | 3/2002 |
| WO | WO 95/05363 | 2/1995 |
| WO | WO 97/06158 | 2/1997 |
| WO | WO 97/36871 | 10/1997 |
| WO | WO 98/05357 | 2/1998 |
| WO | WO 98/06424 | 2/1998 |
| WO | WO 98/06425 | 2/1998 |
| WO | WO 98/24766 | 6/1998 |
| WO | WO 98/34919 | 8/1998 |
| WO | WO 00/01730 | 1/2000 |
| WO | WO 00/18409 | 4/2000 |
| WO | WO 00/18909 | 4/2000 |
| WO | WO 00/22666 | 4/2000 |
| WO | WO 00/50079 | 8/2000 |
| WO | WO 00/75659 | 12/2000 |
| WO | WO 01/49321 | 7/2001 |
| WO | WO01/62272 | 8/2001 |
| WO | WO 01/87328 | 11/2001 |
| WO | WO 02/080893 | 10/2002 |
| WO | WO 03/073981 | 9/2003 |
| WO | WO2004/009776 | 1/2004 |
| WO | WO 2004/032718 | 4/2004 |
| WO | WO2005/011689 | 2/2005 |
| WO | WO2005/039393 | 5/2005 |

OTHER PUBLICATIONS

U.S. Appl. No. 09/980,784.
U.S. Appl. No. 11/788,651, filed Apr. 20, 2007.
U.S. Appl. No. 60/585,735, filed Jul. 6, 2004.
U.S. Appl. No. 60/760,236, filed Jan. 18, 2006.
U.S. Appl. No. 60/738,331, filed Nov. 18, 2005.
Amin et al., "A novel mechanism of action of tetracyclines: Effects on nitric oxide synthases," *Proc. Natl. Acad. Sci. USA*, 1996, 93:14014-14019.
Aoki et al., "Local Application of Disc-Related Cytokines on Spinal Nerve Roots," *Spine*, 2002, 27(15):1614-1617.
Arai et al., "Indomethacin blocks the nucleus pulposus-induced effects on nerve root function. An experimental study in dogs with assessment of nerve conduction and blood flow following experimental disc herniation," *Eur. Spine J.*, 2004, 13(8):691-694.
Baumgartner et al., "Constitutive and Inducible Mechanisms for Synthesis and Release of Cytokines in Immune Cell Lines," *J. Immunol.*, 1996, 157:4087-4093.
Bidani and Heming, "Effects of Lidocaine on Cytosolic pH Regulation and Stimulus-Induced Effector Functions in Alveolar Macrophages," *Lung*, 1997, 175:349-361.
Black et al., "A metalloproteinase disintegrin that releases tumour-necrosis factor-α from cells," *Nature*, 1997, 385:729-733.
Bluthé et al., "Interleukin-1 mediates behavioural but not metabolic effects of tumor necrosis factor α in mice," *Eur. J. Pharmacol.*, 1991, 209:281-283.
Boden et al., "Abnormal Magnetic-Resonance Scans of the Lumbar Spine in Asymptomatic Subjects. A prospective investigation," *J. Bone Joint Surg.*, 1990, 72A(3):403-408.

Boos et al., "1995 Volvo Award in Clinical Sciences. The Diagnostic Accuracy of Magnetic Resonance Imaging, Work Perception, and Psychosocial Factors in Identifying Symptomatic Disc Herniations," *Spine*, 1995, 20(24):2613-2625.

Boos et al., "Tissue Characterization of Symptomatic and Asymptomatic Disc Herniations by Quantitative Magnetic Resonance Imaging," *J. Orthop. Res.*, 1997, 15:141-149.

Bourrie et al., "Enhancement of endotoxin-induced interleukin-10 production by SR 31747A, a sigma ligand," *Eur. J. Immunol.*, 1995, 25:2882-2887.

Brattsand and Linden, "Cytokine modulation by glucocorticoids: mechanisms and actions in cellular studies," *Aliment Pharmacol. Ther.*, 1996, 10(suppl 2):81-90.

Brisby et al., "Proinflammatory cytokines in cerebrospinal fluid and serum in patients with disc herniation and sciatica," *Eur. Spine J.*, 2002, 11:62-66.

Brisby et al., "Inflammation in disc herniation may be a response to nucleus pulposus cell cytokine production and not primary infiltration of inflammatory cells," *45th Annual Meeting Orthopaedic Research Society*, Feb. 1-4, 1999, Anaheim, CA, 1 page.

Buck and Cooperman, "Single Protein Omission Reconstitution Studies of Tetracycline Binding to the 30S Subunit of *Escherichia coli* Ribosomes," *Biochemistry*, 1990, 29(22):5374-5379.

Burke et al., "Intervertebral discs which cause low back pain secrete high levels of proinflammatory mediators," *J. Bone Joint Surg. Br.*, 2002, 84:196-201.

Burke et al., "Spontaneous Production of Monocyte Chemoattractant Protein-1 and Interleukin-8 by the Human Lumbar Intervertebral Disc," *Spine*, 2002, 27(13):1402-1407.

Byröd et al., "A Rapid Transport Route Between the Epidural Space and the Intraneural Capillaries of the Nerve Roots," *Spine*, 1995, 20(2):138-143.

Byröd et al., "Methylprednisolone Reduces the Early Vascular Permeability Increase in Spinal Nerve Roots Induced by Epidural Nucleus Pulposus Application," *J. Orthop. Res.*, 1987, 18:983-987.

Chao et al., "Interleukin-1 and Tumor Necrosis Factor-α Synergistically Mediate Neurotoxicity; Involvement of Nitric Oxide and of N-Methyl-D-aspartate Receptors," *Brain Behav. Immun.*, 1995, 9:355-365.

Chapple et al., "Structure-Function Relationship of Antibacterial Synthetic Peptides Homologous to a Helical Surface Region on Human Lactoferrin against *Escherichia coli* Serotype O111," *Infection and Immunity*, 1998, 66(6):2434-2440.

Chin et al., "Etanercept (Enbrel®) therapy for chronic inflammatory demyelinating polyneuropathy," *J. Neurol. Sci.*, 2003, 210:19-21.

Cornefjord et al., "Nucleus pulposus-induced nerve root injury: effects of diclofenac and ketoprofen," *Eur. Spine J.*, 2002, 11:57-61.

Crickmore and Salmond, "The *Escherichia coli* heat shock regulatory gene is immediately downstream of a cell division operon: the fam mutation is allelic with rpoH," *Mol. Gen. Genet.*, 1986, 205:535-539.

Dawson et al., "Cyclosporin A inhibits the in vivo production of interleukin-1β and tumour necrosis factor α, but not interleukin-6, by a T-cell-independent mechanism," *Cytokine*, 1996, 8(12):882-888.

DeLeo et al., "Cytokine and growth factor immunohistochemical spinal profiles in two animal models of mononeuropathy," *Brain Res.*, 1997, 759:50-57.

Dhainaut et al., "CDP571, a humanized antibody to human tumor necrosis factor-α Safety, Pharmacokinetics, immune response, and influence of the antibody on cytokine concentrations in patients with septic shock," *Crit. Care Med.*, 1995, 23(9):1461-1469.

Dick et al., "Neutralizing TNF-alpha Activity Modulates T-cell Phenotype and Function in Experimental Autoimmune Uveoretinitis," *J. Autoimmunity*, 1998, 11(3):255-264.

"Development of Enbrel® (etanercept)," http://www.enbrel.com/rheumatology/enbrel-rhcpabout-devel.jsp, printed Oct. 19, 2005, 2 pages.

Gadient et al., "Interleukin-1 β and tumor necrosis factor-α synergistically stimulate nerve growth factor (NGF) release from cultured rat astrocytes," *Neurosci. Lett.*, 1990, 117:335-340.

García-Vicuña et al., "Prevention of Cytokine-induced changes in leukocyte adhesion receptors by nonsteroidal antiinflammatory drugs from the oxicam family," *Arthritis Rheum.*, 1997, 40:143-153.

Gearing et al., "Processing of tumour necrosis factor-α precursor by metalloproteinases," *Nature*, 1994, 370:555-557.

Gelderd et al., "The Effects of Interleukin-1 Receptor Antagonist Protein (IRAP) Infusion Following Spinal Cord Transection in Rats," *Mol. Chem. Neuropathol.*, 1996, 27(2):167-183.

Gill and Salmond, "The identification of the *Escherichia coli fts Y* gene product: an unusual protein," *Mol. Microbiol.*, 1990, 4(4):575-583.

Goetzl et al., "Matrix Metalloproteinases in Immunity," *J. Immunol.*, 1996, 156:1-4.

Gonzalez et al., "Long-term effect of nonsteroidal anti-inflammatory drugs on the production of cytokines and other inflammatory mediators by blood cells of patients with osteoarthritis," *Agents Actions*, 1994, 41:171-178.

Hartung et al., "Inflammatory mediators in demyelinating disorders of the CNS and PNS," *J. Neuroimmunol.*, 1992, 40:197-210.

Hattori et al., "Tumor necrosis factor is markedly synergistic with interleukin I and interferon-γ in stimulating the production of nerve growth factor in fibroblasts," *FEBS Lett.*, 1994, 340:177-180.

Herman et al., "Nonsteroidal Antiinflammatory Drug Modulation of Prosthesis Pseudomembrane Induced Bone Resorption," *J. Rheumatol.*, 1994, 21:338-343.

Homma et al., "A comparison of chronic pain behavior following local application of tumor necrosis factor α to the normal and mechanically compressed lumbar ganglia in the rat," *Pain*, 2002, 95:239-246.

Igarashi et al., "2000 Volvo Award Winner in Basic Science Studies: Exogenous Tumor Necrosis Factor-Alpha Mimics Nucleus Pulposus-Induced Neuropathology. Molecular, Histologic, and Behavioral Comparisons in Rats," *Spine*, 2000, 26(23):2975-2980.

Iwabuchi et al., "Effects of Anulus Fibrosus and Experimentally Degenerated Nucleus Pulposus on Nerve Root Conduction Velocity," *Spine*, 2001, 26(15):1651-1655.

Iwamoto and Takeda, "Possible cytotoxic mechanisms of TNF in vitro," *Hum. Cell.*, 1990, 3:107-112 (English summary attached).

Jeanjean et al., "Interleukin-1β induces long-term increase of axonally transported opiate receptors and substance P," *Neuroscience*, 1995, 68(1):151-157.

Jurd et al., "Endothelial cell activation in cutaneous vasculitis," *Clin. Exp. Dermatol.*, 1996, 21:28-32.

Karppinen et al., "Treatment of Sciatica with Infliximab, a monoclonal humanised chimaeric antibody against TNF-α," *J. Bone Joint Surg.*, 2004, 86B(suppl 3):341-342, Abstract O3057.

Karppinen et al., "Tumor Necrosis Factor-α Monoclonal Antibody, Infliximab, Used to Manage Severe Sciatica," *Spine*, 2003, 28(8):750-754.

kawakami et al., "mRNA Expression of Interleukins, Phospholipase $A_2$, and Nitric Oxide Synthase in the Nerve Root and Dorsal Root Ganglion Induced by Autologous Nucleus Pulposus in the Rat," *J. Orthopaedic Res.*, 1999, 17:941-946.

Kawakami et al., "Pathomechanism of Pain-Related Behavior Produced by Allografts of Intervertebral Disc in the Rat," *Spine*, 1996, 21(18):2101-2107.

Kayama et al., "Incision of the Anulus Fibrosus Induces Nerve Root Morphologic, Vascular, and Functional Changes. An experimental study," *Spine*, 1996, 21(22):2539-2543.

Kayama et al., "Cultured, Autologous Nucleus Pulposus Cells Induce Functional Changes in Spinal Nerve Roots," *Spine*, 1998, 23(20):2155-2158.

Kloppenburg et al., "The Tetracycline Derivative Minocycline Differentially Affects Cytokine Production by Monocytes and T Lymphocytes," *Antimicrob. Agents Chemother.*, 1996, 40(40):934-940.

Kloppenburg et al., "The influence of tetracyclines on T cell activation," *Clin. Exp. Immunol.*, 1995, 102:635-641.

Klusman and Schwab, "Effects of pro-inflammatory cytokines in experimental spinal cord injury," *Brain Res.*, 1997, 762:173-184.

"The body's own toxoids help in therapy," Dec. 12, 1999, http://www.rp-online.de/news/wissenschaft/1999-1230/bandscheibenvorfall.html, translation included.

Köller et al., "Immunologically induced electrophysiological dysfunction: Implications for inflammatory diseases of the CNS and PNS," *Prog. Neurobiol.*, 1997, 52:1-26.

Kraemer et al., "Lumbar epidural perineural injection: a new technique," *Eur. Spine J.*, 1997, 6(5):357-361.

Lamster et al., "The effect of tetracycline fiber therapy on β-glucuronidase and interleukin-1β in crevicular fluid," *J. Clin. Periodontol.*, 1996, 23:816-822.

Liberski et al., "Further ultrastructural studies of lesions induced in the optic nerve by Tumor necrosis factor alpha (TNF-α): a comparison with experimental Creutzfeldt-Jakob disease," *Acta Neurobiol. Exp.*, 1994, 54:209-218.

Lin et al., "An immunohistochemical study of TNF-α in optic nerves from AIDS patients," *Curr. Eye Res.*, 1997, 16:1064-1068.

Liu et al., "Increased Sensitivity of Sensory Neurons to Tumor Necrosis Factor α in Rats with Chronic Compression of the Lumbar Ganglia," *J. Neurophysiol.*, 2002, 88:1393-1399.

Lorenz and Kalden, "Biological Agents in Rheumatoid Arthritis," *BioDrugs*, 1998, 9(4):303-324.

Madigan et al., "Tumor necrosis factor-alpha (TNF-α)-induced optic neuropathy in rabbits," *Neurol. Res.*, 1996, 18:176-184.

Malcangio et al., "Effect of interleukin-1β on the release of substance P from rat isolated spinal cord," *Eur. J. Pharmacol.*, 1996, 299:113-118.

Matsumori et al., "Amiodarone Inhibits Production of Tumor Necrosis Factor-$_\alpha$ by Human Mononuclear Cells. A Possible Mechanism for its Effect in Heart Failure," *Circulation*, 1997, 96:1386-1389.

Milano et al., "Intraperitoneal Injection of Tetracyclines Protects Mice from Lethal Endotoxemia Downregulating Inducible Nitric Oxide Synthase in Various Organs and Cytokine and Nitrate Secretion in Blood," *Antimicrob. Agents Chemother.*, 1997, 41:117-121.

Mixter and Barr, "Rupture of the intervertebral disc with involvement of the spinal canal," *New Eng. Surg. Soc.*, 1934, 211(6):210-215.

Moelling, "DNA for genetic vaccination and therapy," *Cytokines Cell. Mol. Ther.*, 1997, 3(2):127-136.

Nawroth et al., "Tumor necrosis factor/cachectin-induced intravascular fibrin formation in meth A fibrosarcomas," *J. Exp. Med.*, 1988, 168:637-647.

Nishi et al., "DNA Sequence and Complementation Analysis of a Mutation in the rp/X Gene from *Escherichia coli* Leading to Loss of Ribosomal Protein L24," J. Bacteriol., 1985, 163(3):890-894.

Odell et al., "Antibacterial activity of peptides homologous to a loop region in human lactoferrin," *FEBS Lett.*, 1996, 382:175-178.

Oka et al., "Intracerebroventricular Injection of Tumor Necrosis Factor-α Induces Thermal Hyperalgesia in Rats," *Neuroimmunomodulation*, 1996, 3:135-140.

Olmarker et al., "Inflammatogenic Properties of Nucleus Pulposus," *Spine*, 1995, 20(6):665-669.

Olmarker et al., "The Effects of Normal, Frozen, and Hyaluronidase-Digested Nucleus Pulposus on Nerve Root Structure and Function," *Spine*, 1997, 22(5):471-476.

Olmarker et al., "Effects of Methylprednisolone on Nucleus Pulposus-Induced Nerve Root Injury," *Spine*, 1994, 19(16):1803-1808.

Olmarker and Larsson, "Tumor Necrosis Factor α and Nucleus-Pulposus-Induced Nerve Root Injury," *Spine*, 1998, 23(23): 2538-2544.

Olmarker and Myers, "Pathogenesis of sciatic pain: role of herniated nucleus pulposus and deformation of spinal nerve root and dorsal root ganglion," *Pain*, 1998, 78(2):99-105.

Olmarker et al., "Ultrastructural Changes in Spinal Nerve Roots Induced by Autologous Nucleus Pulposus," *Spine*, 1996, 21(4):411-414.

Olmarker and Rydevik, "Selective Inhibition of Tumor Necrosis Factor-α Prevents Nucleus Pulposus-Induced Thrombus Formation, Intraneural Edema, and Reduction of Nerve Conduction Velocity. Possible Implications for Future Pharmacologic Treatment Strategies of Sciatica," *Spine*, 2001, 26(8):863-869.

Olmarker et al., "Autologous Nucleus Pulposus Induces Neurophysiologic and Histologic Changes in Porcine Cauda Equina Nerve Roots," *Spine*, 1993, 18(11):1425-1432.

Onda et al., "Exogenous Tumor Necrosis Factor-α Induces Abnormal Discharges in Rat Dorsal Horn Neurons," *Spine*, 2002, 27(15):1618-1624.

Otani et al., "Nucleus Pulposus-induced Nerve Root Injury: Relationship between Blood Flow and Motor Nerve Conduction Velocity," *Neurosurgery*, 1999, 45(3):614-620.

Pennica et al., "Cardiotrophin-1, a Cytokine Present in Embryonic Muscle, Supports Long-Term Survival of Spinal Motoneurons," *Neuron*, 1996, 17:63-74.

Person, "Dermatomyositis responding to pentosifylline," *Br. J. Dermatol.*, 1995, 134(3):593.

Petrovich et al., "Pentoxifylline suppression of TNF-α mediated axonal degeneration in the rabbit optic nerve," *Neurol. Res.*, 1997, 19:551-554.

Pichler et al., "High IL-5 Production by Human Drug-Specific T Cell Clones," *Int. Arch. Allergy Immunol.*, 1997, 113:177-180.

Plata-Salaman et al., "Interleukin-1β enhances spinal cord blood flow after intrathecal administration in the normal rat," *Am. J. Physiol.*, 1995, 269:R1032-R1037.

Rand et al., "Murine Nucleus Pulposus-Derived Cells Secrete Interleukins-1-β, -6, and -10 and Granulocyte-Macrophage Colony-Stimulating Factor in Cell Culture," *Spine*, 1997, 22(22):2598-2601.

Redford et al., "Vascular changes and demyelination induced by the intraneural injection of tumour necrosis factor," *Brain*, 1995, 118:869-878.

Reinecke et al., The Use of Interleukin-1-Receptor Antagonist (IL-1 ra) in the Treatment of the "Lumbar Facet Syndrome," ISSLS, Abstracts 2000, Adelaide, Australia, Abstract 173.

Reinecke et al., "In vitro Transfer of Genes into Spinal Tissues," *Z. Orthop.*, 1997, 135(5):412-416 (English summary included).

Robache-Gallea et al., "Partial purification and characterization of a tumor necrosis factor-α converting activity," *Eur. J. Immunol.*, 1997, 27:1275-1282.

Rosendahl et al., "Identification and Characterization of a Pro-tumor Necrosis Factor-α-processing Enzyme from the Adam Family of Zinc Metalloproteases," *J. Biol. Chem.*, 1997, 272(39):24588-24593.

Rost, "Twilight zone of protein sequence alignments," *Protein Engineering*, 1999, 12(2):85-94.

Rowin et al., "Etanercept treatment in corticosteroid-dependent *Myasthenia gravis*," Neurology, 2004, 63:2390-2392.

Rydevik et al., "Effects of graded compression and nucleus pulposus on nerve tissue: an experimental study in rabbits," *Acta Orthop. Scand.*, 1983, 54:670-671.

Safieh-Garabedian et al., "Contribution of interleukin-1β to the inflammation-induced increase in nerve growth factor levels and inflammatory hyperalgesia," *Brit. J. Pharmacol.*, 1995, 115(7):1265-1275.

Safieh-Garabedian et al., "Involvement of Interleukin-1β, Nerve Growth Factor, and Prostaglandin-$E_2$ in the Hyperalgesia Induced by Intraplantar Injections of Low Doses of Thymulin," *Brain Behav. Immun.*, 1997, 11(3):185-200.

Safieh-Garabedian et al., "Zinc Reduces the Hyperalgesia and Upregulation of NGF and IL-1β Produced by Peripheral Inflammation in the Rat," *Neuropharmacol.*, 1996, 35(5):599-603.

Said and Hontebeyrie-Joskowicz, "Nerve lesions induced by macrophage activation," *Res. Immunol.*, 1992, 143:589-599.

Schäfers et al., "Combined epineurial therapy with neutralizing antibodies to tumor necrosis factor-alpha and interleukin-1 receptor has an additive effect in reducing neuropathic pain in mice," *Neurosci. Lett.*, 2001, 310:113-116.

Schenk and Reiter, "Intrathecal cortison injection in lumbar disc problems," *Arch. Orthopadische Und Unfall-Chirurgie*, 1976, 85(1):21-31 (English abstract).

Schlumpf and Johr, "Acute lumbar disk displacement with nerve root compression. Indications for peridural steroid injection," *Schweizerische Rundschau Fur Medizin Praxis*, 1997, 86(8):292-295.

Seekamp et al., "Requirements for tumor necrosis factor-alpha and interleukin-1 in limb ischemia/reperfusion injury and associated lung injury," *Am. J. Pathol.*, 1993, 143(2):453-463.

Selmaj and Raine, "Tumor Necrosis Factor Mediates Myelin and Oligodendrocyte Damage In Vitro," *Ann. Neurol.*, 1988, 23:339-346.

Shapira et al., "Human Monocyte Response to Cementum Extracts From Periodontally Diseased Teeth: Effect of Conditioning With Tetracycline," *J. Periodontol.*, 1996, 67:682-687.

Shapira et al., "Tetracycline inhibits *Porphyromonas gingivalis* lipopolysaccharide-induced lesions in vivo and TNFα processing in vitro," *J. Periodont. Res.*, 1997, 32:183-188.

Sharief et al., "Circulating Tumor Necrosis Factor-α Correlates with Electrodiagnostic Abnormalities in Guillain-Barré Syndrome," *Ann. Neurol.*, 1997, 42:68-73.

Sharma et al., "Topical application of TNF-α antiserum attenuates spinal cord trauma induced edemaformation, microvascular permeability disturbances and cell injury in the rat," *Acta Neurochir*, 2003, 86(suppl):1-7.

Shinmei et al., "The Role of Interleukin-1 on Proteoglycan Metabolism of Rabbit Annulus Fibrosus Cells Cultured In Vitro," *Spine*, 1988, 13(11):1284-1290.

Skouen et al., "Protein Markers in Cerebrospinal Fluid in Experimental Nerve Root Injury. A study of slow-onset chronic compression effects or the biochemical effects of nucleus pulposus on sacral nerve roots," *Spine*, 1999, 24(21):2195-2200.

Smith, "Microbial pathogen genomes-new strategies for identifying therapeutics and vaccine targets," *Tibtech*, 1996, 14:290-293.

Smith et al., "Cyclosporin A blocks induction of tumor necrosis factor-alpha in human B lymphocytes," *Biochem. Biophys. Res. Commun.*, 1994, 204:383-390.

Smolen et al., "Efficacy and safety of leflunomide compared with placebo and sulphasalazine in active rheumatoid arthritis: a double-blind, randomized, multicentre trail," *Lancet*, 1999, 353:259-266.

Sommer et al., "A metalloprotease-inhibitor reduces pain associated behavior in mice with experimental neuropathy," *Neurosci. Letters*, 1997, 237:45-48.

Sommer et al., "The effect of thalidomide treatment on vascular pathology and hyperalgesia caused by chronic constriction injury of rat nerve," *Pain*, 1998, 74:83-91.

Sommer et al., "Etanercept reduces hyperalgesia in experimental painful neuropathy," *J. Peripheral Nerve Syst.*, 2001, 6:67-72.

Sorkin et al., "Tumour necrosis factor-α induces ectopic activity in nociceptive primary afferent fibres," *Neuroscience*, 1997, 81:255-262.

Steinmeyer et al., "Pharmacological Effect of Tetracyclines on Proteoglycanases from Interleukin-1-Treated Articular Cartilage," *Biochem. Pharmacol.*, 1998, 55:93-100.

Stephens and Shapiro, "Bacterial protein secretion-a target for new antibiotics?" *Chem. Biol.*, 1997, 4(9):637-641.

Stoll et al., "Tumor necrosis factor-α in immune-mediated demyelination and Wallerian degeneration of the rat peripheral nervous system," *J. Neuroimmunol.*, 1993, 45:175-182.

Szlosarek and Balkwill, "Tumour necrosis factor œ a potential target for the therapy of solid tumours," *Lancet Oncol.*, 2003, 4:565-573.

Takahashi et al., "Inflammatory Cytokines in the Herniated Disc of the Lumbar Spine," *Spine*, 1996, 21(2):218-224.

Takao et al., "Lidocaine attenuates hyperoxic lung injury in rabbits," *Acta Anaesthesiol. Scand.*, 1996, 40:318-325.

Teoh et al., "Steroid Inhibition of Cytokine-Mediated Vasodilation After Warm Heart Surgery," *Circulation*, 1995, 92(suppl 2):II-347-II-353.

Tobinick and Davoodifar, "Perispinal TNF-alpha inhibition for discogenic pain," *Swiss Med. Wkly.*, 2003, 133:170-177.

Tobinick and Davoodifar, "Efficacy of etanercept delivered by perispinal administration for chronic back and/or neck disc-related pain: a study of clinical observations in 143 patients," *Curr. Med. Res. Opin.*, 2004, 20(7):1075-1085.

Tobinick, "Targeted Etanercept for Discogenic Neck Pain: Uncontrolled, Open-Label Results in Two Adults," *Clin. Ther.*, 2003, 25:1211-1218.

Tobinick, "Targeted Etanercept for Treatment-Refractory Pain Due to Bone Metastasis: Two Case Reports," *Clin. Thera.*, 2003, 25(8):2279-2288.

Tsukamoto et al., "Suppressive effects of TNF-α on myelin formation in vitro," *Acta Neurol. Scand.*, 1995, 91:71-75.

van de Poll et al., "Tumor Necrosis Factor-α Induces Activation of Coagulation and Fibrinolysis in Baboons Through an Exclusive Effect on the p55 Receptor," *Blood*, 1996, 88(3):922-927.

Villarroya et al., "Myelin-induced experimental allergic encephalomyelitis in Lewis rats: tumor necrosis factor α levels in serum of cerebrospinal fluid Immunohistochemical expression in glial cells and macrophages of optic nerve and spinal cord," *J. Neuroimmunol.*, 1996, 64:55-61.

Wacnik et al., "Nociceptive Characteristics of Tumor Necrosis Factor-α in Naïve and Tumor-Bearing Mice," *Neuroscience*, 2005, 132:479-491.

Wagner and Myers, "Schwann cells produce tumor necrosis factor alpha: expression in injured non-injured nerves," *Neuroscience*, 1996, 73(3):625-629.

Wagner and Myers, "Endoneurial injection of TNF-α produces neuropathic pain behaviors," *NeuroReport*, 1996, 7:2897-2901.

Wang et al., "Production of tumor necrosis factor in spinal cord following traumatic injury in rats," *J. Neuroimmunol.*, 1996, 69:151-156.

Wasaki et al., "Preventive effect of cyclosporin A on experimentally induced acute liver injury in rats" *Liver*, 1997, 17:107-114.

Wehling, "Antizytokine gegen entzundung und schmerz (Anticytokines against inflamation and pain)," Orthopadische Nachrichten, 1998, p. 16, Biermann Verlag GmbH, Koln, Germany, http://www.arthrose-ischias.de/ftp/presse 2.pdf, translation included.

Wehling et al., "Epidural Injections with Interleukin-1-Receptor-Antagonist-Protein (IRAP) in Lumbar Radicular Compression: Pathophysiological Background, Safety and Clinical Results," *Int. Soc. Study Lumbar Spine*, 1998, p. 16.

Wehling et al., Information Orthokin, "Die behandlung von eshias, arthrose und rheumatoider arthrisis mit orthokin®," Wissenschaftliche Informationen (Patient Information Paper), relevant portions translated.

Wehling et al., "Neurophysiologic Changes in Lumbar Nerve Root Inflammation in the Rat After Treatment with Cytokine Inhibitors: Evidence for a Role of Interleukin-1," *Spine*, 1996, 21(8):931-935.

Wehling et al., "The Effect of Cytokines on Regeneration of Compressed Nerve Roots and Transsected Peripheral Nerves," *Z. Orthop.*, 1993, 131:83-93 (English summary included).

Wehling et al., "The interaction between synovial cytokines and peripheral nerve function: a possible element in the development of radicular syndromes," *Z. Orthop.*, 1990, 128(5):442-446 (English summary included).

Wehling, "The Use of Cytokine Antagonists in the Treatment of Lumbar Radicular Compression: Pathophysiological Background, Safety and 3 Year Clinical Experience," *Abstr. Int. Soc. Study Lumbar Spine*, Adelaide, Australia, Apr. 9-13, 2000, Abstract 38.

Wehling et al., "Transfer of Genes to Chondrocytic Cells of the Lumbar Spine: Proposal for a Treatment Strategy of Spinal Disorders by Local Gene Therapy," *Spine*, 1997, 22(10):1092-1097.

Wehling, Wissenschaftliches programm (Scientific Program), Jun. 18, 1999, "Epidural injection with a new autologous interleukin-1 receptor-antagonist-protein (IL-1 ra) at radicular compression: pathophysiology, safety and clinical results," http://medweb.uni-muenster.de/institute/orth/versanstaltungen/99-06-18v.html, relevant portions translated.

Weilbach and Gold, "Disease Modifying Treatments for Multiple Sclerosis. What Is On the Horizon?" *CNS Drugs*, 1999, 11(2):133-157.

Weinblatt et al., "A trial of Etanercept, a recombinant tumor necrosis factor receptor: Fc fusion protein, in patients with rheumatoid arthritis receiving methotrexate," *N. Engl. J. Med.*, 1999, 340(4):253-259.

Wershil et al., "Dexamethasone Cyclosporin A Suppress Mast Cell-Leukocyte Cytokine Cascades by Multiple Mechanisms," *Int. Arch. Allergy Immunol.*, 1995, 107:323-324.

Wiesel et al., "1984 Volvo Award in Clinical Sciences. A Study of Computer-Assisted Tomography. I. The Incidence of Positive CAT Scans in an Asymptomatic Group of Patients," *Spine*, 1984, 9(6):549-551.

Willison and Tissot, "The *Escherichia coli efg* Gene and the *Rhodobacter capsulatus adgA* Gene Code for $NH_3$-Dependent NAD Synthetase," J. Bacteriol., 1994, 176(11):3400-3402.

Woolf et al., "Cytokines, nerve growth factor and inflammatory hyperalgesia: the contribution of tumour necrosis factor α" *Br. J. Pharmacol.*, 1997, 121(3):417-424.

Wower et al., "Ribosomal Protein L27 Participates in both 50 S Subunit Assembly and the Peptidyl Transferase Reaction," *J. Biol. Chem.*, 1998, 273(31):19847-19852.

Yabuki et al., "Effects of Lidocaine on Nucleus Pulposus-Induced Nerve Root Injury," *Spine*, 1998, 23(22):2383-2390.

Yabuuchi et al., "Biphasic effects of intra intracerebroventricular interleukin-1 β on mechanical nociception in the rat," *Eur. J. Pharmacol.*, 1996, 300:59-65.

Zhu et al., "Cytokine Dichotomy in Peripheral Nervous System Influences the Outcome of Experimental Allergic Neuritis: Dynamics of mRNA Expression for IL-1β, IL-6, IL -10, IL-12, TNF-αTNF-β, and Cytolysin," *Clin. Immunol. Immunopathol.*, 1997, 84:85-94.

Zanella et al., "Effect of Etanercept, a Tumor Necrosis Factor-Alpha Inhibitor, on Neuropathic Pain in the Rat Chronic Constriction Injury Model," *Spine*, 2008, 33(3):227-234.

Autio et al., "The Effect of Infiximab, a Monoclonal Antibody Against TNF-a, on Disc Herniation Resorption," *Spine*, 31(23); pp. 2641-2645, (2006).

Arden et al., "A multicentre randomized controlled trial of epidural corticosteroid injections for sciatica: the West study," *Rheumatology*, 44; pp. 1399-1406, (2005).

Brennan et al., "Treating Sciatica with Adalimumab: A Pilot Study," *SAT0146*, 1 page (2004).

Buttermann, "Treatment of Lumbar Disc Herniation: Epidural Steroid Injection Compared with Discectony. A Prospective, Randomized Study," *JB&JS*, p. 670, (2006).

Carette et al., "Epidural Corticosteroid Injections for Sciatica Due to Herniated Nucleus Pulposus," *New England J. of Med.*, p. 1634, (1997).

Cohen, "A Double-Blind, Placebo-controlled, Dose-Response Pilot Study Evaluating Intradiscal Etanercept in Patients with Chronic Discogenic Low Back Pain or Lumbosacral Radiculopathy," *Anesthesiology*, 107, pp. 99-105 (2007).

Cyteval et al, "Predictive Factors of Efficacy of Periradicular Corticosteroid Injections for Lumbar Radiculopathy," *AJNR*, 27; p. 978, (2006).

Deyo, "Back Surgery—Who Needs It?" *Massachusetts Medical Society*, p. 2239, (2007).

Finckh et al., "Short-Term Efficacy of Intravenous Pulse Glucocorticoids in Acute Discogenic Sciatica. A Randomized Controlled Trial," *Spine*, 31(4); pp. 377-381, (2006).

Galley et al, "The immuno-inflammatory cascade," *British J. of Anaesthesia*, 77; pp. 11-16, (1996).

Genevay et al., "Efficacy of etanercept in the treatment of acute, severe sciatica: a pilot study," *Ann. Rheum. Dis.*, 63; pp. 1120-1123, (2004).

Heyde et al., "Trauma induces apoptosis in human thoracolumbar intervertebral discs," *BMC Clinical Path.*, 6(5); 9 pages, (2006).

Karpinen et al., "Periradicular Infiltration for Scatica," *Spine*, 26(9); pp. 1059-1067, (2001).

Korhonen, "The Treatment of Disc Herniation-Induced Sciatica With Infliximab," *Spine*, (31):24, pp. 2759-2766, (2006).

Korhonen et al, "The Efficacy of Infliximab for Disc Herniation-Induced Sciatica. A 1-Year Follow-Up of First II, A Randomised Controlled Trial," 1 page, (2004).

Korhonen et al, "Efficacy of Infiximab for Disc Herniation-Induced Sciatica," *Spine*, 29(19); pp. 2115-2119, (2004).

Korner et al, "Critical Points of Tumor Necrosis Factor Action in Central Nervous System Autoimmune Inflammation Defined by Gene Targeting," *J. Exp. Med.*, 186(9); pp. 1585-1590, (1997).

Lin et al, "Cervical Epidural Steroid Injections for Symptomatic Disc Herniations," *J. Spinal Disord. Tech.*, 19(3); p. 183, (2005).

Lundin, "Corticosteroids in Lumbar Disc Surgery," *Eur. Spine J.*, 12; pp. 625-630, (2003).

Ohtori et al, "Tumor Necrosis Factor-Immunoreactive Cells and PGP 9.5-Immunoreactive Nerve Fibers in Vertebral Endplates of Patients with Discogenic Low Back Pain and Modic Type 1 or Type 2 Changes on MRI," *Spine*, 31(9); pp. 1026-1031, (2006).

Raoul et al., "Chronic activation in presymptomatic amyotrophic lateral sclerosis (ALS) mice of a feedback loop involving Fas, Daxx, and FasL," *PNAS*, 103(15); pp. 6007-6012, (2006).

Riew et al, "The Effect of Nerve-Root Injections on the Need for Operative Treatment of Lumbar Radicular Pain: A Prospective, Randomized, Controlled, Double-Blind Study," *JB&JS*, p. 1589, (2000).

Riew et al, "Nerve Root Blocks in the Treatment of Lumbar Radicular Pain. A Minimum Five-Year Follow-Up," *JB&JS*, 82(11); p. 1722, (2006).

"Adult low back pain." *National Guideline Clearinghouse*, [www.guideline.gov], printed 2007.

"Guidelines for the performance of fusion procedures for deganerative disease of the lumbar spine." *National Guideline Clearinghouse*, [www.guideline.gov], printed 2007.

"Guidelines for the performance of fusion procedures for degenerative disease of the lumbar spine. Part 13: injection therapies, low-back pain, and lumbar fusion." *National Guideline Clearinghouse*, [www.guideline.gov], printed 2007.

"Guidelines for the performance of fusion procedures for degenerative disease of the lumbar spine. Part 10: fusion following decompression in patients with stenosis without spondylolisthesis." *National Guideline Clearinghouse*, [www.guideline.gov], printed 2007.

"Guidelines for the performance of fusion procedures for degenerative disease of the lumbar spine. Part 9: fusion in patients with stenosis and spondylolisthesis." *National Guideline Clearinghouse*, [www.guideline.gov], printed 2007.

"Guidelines for the performance of fusion procedures for degenerative disease of the lumbar spine. Part 8: lumbar fusion for disc herniation and radiculopathy." *National Guideline Clearinghouse*, [www.guideline.gov], printed 2007.

"Guidelines for the performance of fusion procedures for degenerative disease of the lumbar spine. Part 7: intractable low-back pain without stenosis or spondylolisthesis." *National Guideline Clearinghouse*, [www.guideline.gov], printed 2007.

"Guidelines for the performance of fusion procedures for degenerative disease of the lumbar spine. Part 6: magnetic resonance imaging and discography for patient selection for lumbar fusion." *National Guideline Clearinghouse*, [www.guideline.gov], printed 2007.

"Guidelines for the performance of fusion procedures for degenerative disease of the lumbar spine. Part 5: correlation between radiographic and functional outcome." *National Guideline Clearinghouse*, [www.guideline.gov], printed 2007.

"Interventional techniques: evidence-based practice guidelines in the management of chronic spinal pain." *National Guideline Clearinghouse*, [www.guideline.gov], printed 2007.

"Low back - lumbar & thoratic (acute & chronic)." *National Guideline Clearinghouse*, [www.guideline.gov], printed 2007.

"Low back pain." *National Guideline Clearinghouse*, [www.guideline.gov], printed 2007.

"Neck and upper back (acute & chronic)." *National Guideline Clearinghouse*, [www.guideline.gov], printed 2007.

"North American Spine Society Phase III: clinical guidelines for multidisciplinary spine care specialists. Spinal stenosis version 1.0." *National Guideline Clearinghouse*, [www.guideline.gov], printed 2007.

Mohler et al., "Soluble tumor necrosis factor (TNF) receptors are effective therapeutic agents in lethal endotoxemia and function simultaneously as both TNF carriers and TNF antagonists," *J. Immunol.*, 1993, 151(3); pp. 1548-1561.

Muto et al., "Treatment of Herniated Lumbar Disc by Intradiscal and Intraforaminal Oxygen-Ozone ($O_2$ -$O_3$ ) Injection," *J. Neuroradiol.*, 2004, 31; pp. 183-189.

Olmarker, Summary of U.S. Appl. No. 09/760,811, filed Jan. 17, 2001 (10 pages).

Scallon, et al, "Functional Comparisons of Different Tumour Necrosis Factor Receptor/IgG Fusion Proteins," *Cytokine*, 1995, 7(8), pp. 759-770.

Scallon, et al., "Binding and Functional Comparisons of Two Types of Tumor Necrosis Factor Antagonists," *The Journal of Pharmcology and Experimental Therapeutics*, 2002, 301(2); pp. 418-426.

Tartaglia, et al., "The two different receptors for tumor necrosis factor mediate distinct cellular responses," *Proc. Natl. Acad. Sci.* 1991, vol. 88, pp. 9292-9296.

Tracey, et al., "Tumor necrosis factor antagonist mechanisms of action: A comprehensive review," *Pharmacology & Therapeutics*, 2008, vol. 117; pp. 244-279.
U.S. Appl. No. 07/670,827, filed Mar. 18, 1991, Le et al.
U.S. Appl. No. 07/853,606, filed Mar. 18, 1992, Le et al.
U.S. Appl. No. 07/943,852, filed Sep. 11, 1992, Le et al.
U.S. Appl. No. 08/010,406, filed Jan. 29, 1993, Scallon et al.
U.S. Appl. No. 08/013,413, filed Feb. 2, 1993, Le et al.
U.S. Appl. No. 08/570,674, filed Dec. 11, 1995, Le et al.
U.S. Appl. No. 08/422,133, filed May 16, 1995, Scallon et al.
U.S. Appl. No. 09/765,978, filed Jan. 18, 2001, Le et al.
U.S. Appl. No. 09/766,536, filed Jan. 18, 2001, Le et al.
U.S. Appl. No. 10/043,450, filed Jan. 10, 2002, Le et al.
U.S. Appl. No. 10/957,543, filed Sep. 30, 2004, Le et al.
U.S. Appl. No. 12/346,737, filed Dec. 30, 2008, Tobinick.
U.S. Appl. No. 12/344,452, filed Dec. 26, 2008, Tobinick.
U.S. Appl. No. 12/344,437, filed Dec. 26, 2008, Tobinick et al.
Krakauer et al., "Doxycycline Is Anti-Inflammatory and Inhibits Staphylococcal Exotoxin-Induced Cytokines and Chemokines," *Antimicrob. Agents and Chemotherapy*, Nov. 2003, vol. 47(11): pp. 3630-3633.
Notice of Allowance mailed Oct. 30, 2009; Canada Patent Application No. 2,342,200.
Office Action mailed Aug. 3, 2009; EP Application No. 07009705.0.
Office Action mailed Nov. 20, 2009; Japan Application No. 2000-571927.
*Curriculum Vitae* of Mark L. Heaney, M.D., Ph.D., Memorial Sloan-Kettering Cancer Center and Weill Medical College of Cornell University Required Format for *Curriculum Vitae* and Bibliography, May 11, 2009 (11 pages).
Development of ENBREL [www.enbrel.com/hcp/enbrel-development.jsp], printed on Sep. 6, 2009 (3 pages).
Enbrel® (etanercept) For Subcutaneous Injection (2 pages) (2000).
Evans, et al., "Protective Effect of 55- but not 75-kD Soluble Tumor Necrosis Factor Receptor-Immunoglobulin G Fusion Proteins in an Animal Model of Gram-negative Sepsis," *J. Exp. Med.*, 1994, 180:2173-2179.
Goupille, et al., "The Role of Inflammation in Disk Herniation — Associated Radiculopathy," *Semin. Arthritis Rheum.*, 1998, 28(1): 60-71.
Furst et al., "Intravenous Human Recombinant Tumor Necrosis Factor Receptor p55-Fc IgG1 Fusion Protein, Ro 45-2081 (Lenercept): Results of a Dose-Finding Study in Rheumatoid Arthritis," *The J. of Rheumatology*, 2003, 30: 2123-2126.
Mohler et al., "Soluble tumor necrosis factor (TNF) receptors are effective therapeutic agents in lethal endotoxemia and function simultaneously as both TNF carriers and TNF antagonists," *J. Immunol.*, 1993, 151(3); pp. 1548-1561.
Olmarker, et al., "Tumor Necrosis Factor α and Nucleus-Pulposus-Induced Nerve Root Injury," *SPINE*, 1998, 23(23): 2538-2544.
Onrust, et al., "Infiximab: A Review of its Use in Crohn's Disease and Rheumatoid Arthritis," *BioDrugs*, 1998, 10(5): 397-422.
Scallon, et al., "Binding and Functional Comparisons of Two Types of Tumor Necrosis Factor Antagonists," *The Journal of Pharmcology and Experimental Therapeutics*, 2002, 301(2); pp. 418-426.
The Lenercept Multiple Sclerosis Study Group and The University of British Columbia MS/MRI Analysis Group, "TNF neutralization in MS: Results of a randomized, placebo-controlled multicenter study," *Neurology*, 1999, 53(3): 457-465.
Sorbera, "Etanercept, Antiarthritic TNF-α Antagonist," *Drugs of the Future*, 1998, 23(9): 951-954.
Weithmann et al., "Effects of tiaprofenic acid on urinary pyridinium crosslinks in adjuvant arthritic rats: Comparison with doxycycline," *Inflamm. Res.*, 1997, 46: 246-252.

USE OF TNF-ALPHA INHIBITORS FOR TREATING A NERVE DISORDER MEDIATED BY NUCLEUS PULPOSUS

This application is a continuation of U.S. patent application Ser. No. 10/225,237, filed on Aug. 22, 2002, now U.S. Pat. No. 7,115,557, which is a continuation-in-part of Ser. No. 09/826,893 filed Apr. 6, 2001, now abandoned, which is a continuation-in-part of U.S. patent application Ser. No. 09/743,852 filed Jan. 17, 2001, now U.S. Pat. No. 6,649,589, which was a National Stage filing under 35 U.S.C. .sctn. 371 of International Application No. PCT/SE99/01671 filed Sep. 23, 1999 which was published in English on Apr. 6, 2000 and claims benefit of Swedish Application Nos. 9803276-6 and 9803710-4 filed respectively on Sep. 25, 1998 and Oct. 29, 1998. These applications are herein incorporated by reference in their entirety for all purposes.

TECHNICAL FIELD

The present invention relates to a method for treating nerve disorders in a mammal or a vertebrate by administering at least two cytokine inhibitors, of which one is preferably a TNF inhibitor. The invention also relates to the use of at least two cytokine inhibitors, of which one is preferably a TNF inhibitor in the preparation of pharmaceutical compositions for the treatment of nerve root injury.

The object of the present invention is to obtain an improved possibility to treat nerve disorders, such as nerve root injury induced by disc herniation, which may turn up e.g. as a radiating pain in the arm or leg (sciatica), as low back pain or as whiplash associated disorder, by blocking disk related cytokines.

BACKGROUND OF THE INVENTION

It is established that conditions such as sciatica and low back pain are due to activation and irritation of intraspinal nervous structures by disk derived substances (Olmarker K, Rydevik B, Nordborg C, Autologous nucleus pulposus induces neurophysiologic and histologic changes in porcine cauda equina nerve roots, Spine 1993; 18(11): 1425-32; Olmarker K, Larsson K, Tumor necrosis factor alpha and nucleus-pulposus-induced nerve root injury, Spine 1998; 23(23): 2538-44; Olmarker K, Rydevik B, Selective inhibition of tumor necrosis factor-alpha prevents nucleus pulposus-induced thrombus formation, intraneural edema, and reduction of nerve conduction velocity: possible implications for future pharmacologic treatment strategies of sciatica, Spine 2001; 26(8) : 863-9). One key substance for inducing such irritation is Tumor Necrosis Factor alpha (TNF or TNF-alpha). TNF is a proinflammatory cytokine that may sensitize a nerve root in a way that when it is simultaneously deformed mechanically, ectopic nerve may be elicited locally and interpreted by the brain as pain in the corresponding dermatome. TNF may also induce a nutritional deficit in the nerve root by increasing the vascular permeability leading to intraneural edema, and by initiating intravascular coagulation by activation of adhesion molecules at the surface of the endothelial cells (Olmarker K, Rydevik B, Selective inhibition of tumor necrosis factor-alpha prevents nucleus pulposus-induced thrombus formation, intraneural edema, and reduction of nerve conduction velocity: possible implications for future pharmacologic treatment strategies of sciatica, Spine 2001 ;26(8): 863-9). Both these mechanisms may subsequently lead to a reduced blood flow with a reduced supply of nutrients and elimination of metabolic waist products. This reduction in nutrition may also induce sciatic pain per se. TNF may also induce low back pain due to local irritation of sensory nerve endings at the surface of the intervertebral disk. This may occur when the nucleus pulposus herniates out into the spinal canal and TNF produced and released from the disk cells may reach the nerve endings.

Disk herniation is a troublesome disorder, which can cause pronounced pain and muscle dysfunction, and thereby loss of ability to work. A herniation may occur in any disk in the spine but herniations in the lumbar and the cervical spine are most common. A disk herniation in the cervical spine may induce radiating pain and muscle dysfunction in the arm, which is generally referred to as cervical rhizopathy. Herniation in the lumbar spine may induce radiating pain and muscle dysfunction in the leg. The radiating pain in the leg is generally referred to as sciatica. Disk herniation will cause trouble to a varying degree, and the pain may last for one or two months or in severe cases up to 6 months. The arm or leg pain that can occur as a result of disk herniation can be very intense and may thus affect the individual patient's whole life situation during the sickness period.

U.S. Pat. No. 5,703,092 discloses the use of hydroxamic acid compounds and carbocyclic acids as metalloproteinase and TNF inhibitors, for the treatment of arthritis and other related inflammatory diseases. No use of these compounds for the treatment of nerve root injuries is disclosed or suggested.

U.S. Pat. No. 4,925,833 discloses the use of tetracyclines to enhance bone protein synthesis and treatment of osteoporosis.

U.S. Pat. No. 4,666,897 discloses inhibition of mammalian collagenolytic enzymes by administering tetracyclines. The collagenolytic activity is manifested by excessive bone resorption, periodontal disease, rheumatoid arthritis, ulceration of cornea, or resorption of skin or other connective tissue collagen.

However, neither this nor U.S. Pat. No. 4,925,833 disclose nerve root injury or the treatment thereof.

It has also been disclosed that selective inhibition may be efficient in reducing sciatic pain (Korhonen K, Karppinen J, Malmivaara A, Paimela L, Kyllonen E, Lindgren K-A, et al. Treatment of sciatica with infliximab, a monoclonal humanised chimaeric antibody against TNF. Trans. International Society for the Study of the Lumbar Spine 2002; Cleveland, Ohio, p. 14).

Low back pain affects approximately 80% of the population during their lifetime in most countries. Except for being extremely common, it is also one of the most costly disorders for the society. In Sweden alone, low back pain was estimated to cost $320,000,000 in 1997. The major part of the cost relates to indirect costs such as sick-compensation compensation and reduced productivity, and only a minor part is related to direct costs such as medical care and pharmacological substances.

In a minority of the cases (5%), there may be a known cause for the pain such as intra spinal tumors, rheumatic diseases, infections and more. In these cases the treatment may be specifically aimed at the cause. However, in the majority of the cases of low back pain, the cause remains unknown. At present there is no direct way to treat low back pain with an unknown cause and existing treatment modalities only aim at symptomatic relief.

Low Back Pain and Sciatica

It is necessary to make a distinction between low back pain and one specific condition that is often linked to low back pain called "sciatica". Sciatica refers to radiating pain into the leg according to the dermatomal innervation area of a specific spinal nerve root. The pain in sciatica is distinctly different from that of low back pain. In sciatica, the pain is sharp and intense, often described as "toothache-like", and radiates down into the lower extremities, below the level of the knee. The experience of the pain is closely related to the dermatomal innervation of one or more lumbar spinal nerve roots. Sciatica is also frequently related to neurological dysfunction in that specific nerve and may be seen as sensory dysfunction, reduced reflexes and reduced muscular strength. The sciatic pain thus seem to be a neuropathic pain, i.e. pain due to nerve injury, induced by sensitized axons in a spinal nerve root at the lumbar spinal level. The pain experienced by the patient at low back pain is more dull and is diffusely located in the lower back. There is never any radiating pain into the leg.

Sciatica is the result of nerve injury, and the cause of sciatica has an anatomical correlate. Since 1934, sciatica is intimately linked to the presence of a herniated intervertebral disc. However, although most patients with sciatica will display a herniated disc at radiological examination, it is surprising that approximately 30% of an adult population at the age of 40-50 years of age with no present or previous sciatica also have disc herniations when assessed by magnetic resonance tomography, so called "silent" disc herniations (Wiesel, Tsourmas et al. 1984; Boden, Davis et al. 1990; Boos, Rieder et al. 1995; Boos, Dreier et al. 1997). The presence of silent disc herniations is intriguing to the spine research community and seems to contradict the relationship between disc herniations and sciatica.

Scientific Knowledge of the Pathophysiologic Mechanisms Behind Low Back Pain

It is well known that the outer part of the annulus fibrosus of the intervertebral disc and the posterior longitudinal ligament are innervated by C-fibers. Although there are no nerve fibers in the deeper part of the annulus fibrosus or the nucleus pulposus in normal discs, nerves may reach these parts in degenerated discs through annular tears.

Silent Disc Herniations

As presented earlier, it is known that approximately one-third of a normal adult population who never suffered from sciatica have radiological visible disc herniations. Since the presence of a disc herniation is so intimately linked to the symptom of sciatica this is surprising, and at present there is no valid explanation for this phenomenon. However, "silent" in this regard only implies that the disc herniations did not produce sciatica. One may assume though that they produce other symptoms.

Whiplash and Whiplash Associated Disorders (WAD)

About 10% to 20% of the occupants of a stricken vehicle in rear-end car collisions suffer from whiplash injury. The injury may also occur as a result of other types of accidents, such as train accidents, and sudden retardations. This injury is defined as a non-contact acceleration-deceleration injury to the head-neck system. It is most often caused by a rear-end car collision and there is no direct impact on the neck.

Presenting symptoms usually include neckpain, headaches, disequilibrium, blurred vision, parenthesize, changes in cognition, fatigue, insomnia and hypersensitivity to light and sound. Dizziness described in a variety of terms such as imbalance, light-headedness and vertigo also occur frequently and these symptoms may be associated with long-term disability.

Although neurologic and orthopedic examinations do not reveal abnormalities in the majority of patients, the characteristics of dizziness due to whiplash can be elucidated by means of ElectroNystagmoGraphic (ENG) evaluation. This examination is a method that is suitable for proving pathology in the oculo-vestibular system of whiplash-patients.

Until recently, the reason for the extent of injury was poorly understood. In addition, due to the legal and insurance issues, the veracity of complaints of neck pain and other symptoms by people who suffer from whiplash is commonly viewed as suspect.

Whiplash injuries can be quite complex and may include a variety of related problems, such as joint dysfunction, and faulty movement patterns, chronic pain and cognitive and higher center dysfunction.

When the cervical spine (neck) is subject to a whiplash injury, there is usually a combination of factors that contribute to the pain. These factors must be addressed individually, while maintaining a "holistic" view of the patient.

The most significant factors may include one or more of the following: joint dysfunction, muscle dysfunction, and faulty movement patterns.

Joint Dysfunction

This occurs when one of the joints in the spine or limbs loses its normal joint play (resiliency and shock absorption). It is detected through motion palpation, a procedure in which the doctor gently moves the joint in different directions and assesses its joint play. When a joint develops dysfunction, its normal range of movement may be affected and it can become painful. In addition, joint dysfunction can lead to a muscle imbalance and muscle pain and a vicious cycle. The loss of joint play can cause abnormal signals to the nervous system (there are an abundance of nerve receptors in the joint). The muscles related to that joint can subsequently become tense or, conversely, underactive. The resulting muscle imbalance can place increased stress on the joint, aggravating the joint dysfunction that already exists.

Muscle Dysfunction

When joint dysfunction develops, muscles are affected. Some muscles respond by becoming tense and overactive, while others respond by becoming inhibited and underactive. In either case, these muscles can develop trigger points. Trigger points are areas of congestion within the muscle where sensitizing compounds accumulate. These sensitizing compounds can irritate the nerve endings within the muscle and produce pain. This pain can occur in the muscle itself or can be referred pain (perceived in other areas of the body). Muscle related mechanisms may also give rise to abnormal signaling to the nervous system. This event can subsequently cause disruption of the ability of the nervous system to properly regulate muscles in other parts of the body, leading to the development of faulty movement patterns.

Faulty Movement Patterns

It is thought that the intense barrage of pain signals from a traumatic injury to the cervical spine can change the way the nervous system controls the coordinated function of muscles. The disruption of coordinated, stable movement is known as faulty movement patterns. Faulty movement patterns cause increased strain in the muscles and joints, leading to pain. They can involve the neck itself or can arise from dysfunction in other areas of the body such as the foot or pelvis. Instability is also considered part of faulty movement patterns. There are 2 types of instability that can occur in whiplash: passive instability-the ligaments of the neck are loosened, and dynamic instability-the nervous system disruption causes a disturbance in the body's natural muscular response to common, everyday forces. As a result of instability, even mild, innocuous activities can become painful.

SUMMARY OF THE INVENTION

It has been found that the use of a TNF-alpha inhibitor, such as a substance selected from the group consisting of metalloproteinase inhibitors excluding methylprednisolone, tetracyclines including chemically modified tetracyclines, quinolones, corticosteroids, thalidomide, lazaroids, pentoxifylline, hydroxamic acid derivatives, carbocyclic acids, napthopyrans, soluble cytokine receptors, monoclonal antibodies towards TNF-alpha, amrinone, pimobendan, vesnarinone, phosphodiesterase inhibitors, lactoferrin and lactoferrin derived analogs, and melatonin are suitable for treatment of spinal disorders and nerve root injury caused by the liberation of TNF-alpha and compounds triggered by the liberation of or presence of TNF-alpha by inhibiting spinal disc TNF-alpha.

These substances are thus suitable for treatment of nerve root injury, and for treatment of sciatica, low back pain (LBP), and whiplash associated disorder (WAD).

TNF is one of many pro-inflammatory substances with similar action, and it is considered as a "major player" in inflammatory events. However, TNF may also in part acts through other pro-inflammatory cytokines such as for instance IL-1, IL-6, FAS, and IFN-gamma.

The present invention is based on the finding that by combining at least two different inhibitors of pro-inflammatory cytokines it is possible to provide an even better treatment of the above-mentioned diseases and conditions.

It is an object of the invention to provide novel and improved methods for inhibiting the action of cytokines for treating of nerve disorders in a subject comprising the step of administering to said subject a therapeutically effective dosage of at least two substances selected from the group consisting of TNF inhibitors, IL-1 inhibitors, IL-6 inhibitors, IL-8 inhibitors, FAS inhibitors, FAS ligand inhibitors, and IFN-gamma inhibitors.

A preferred embodiment of the invention is a method for treatment of a nerve disorder in a subject comprising administering to a subject a therapeutically effective dosage of a TNF inhibitor in combination with a second inhibitor selected from the group consisting of IL-1 inhibitors, IL-6 inhibitors, IL-8 inhibitors, FAS inhibitors, FAS ligand inhibitors, and IFN-gamma inhibitors.

Another preferred embodiment of the invention is a method for treatment of a nerve disorder in a subject comprising administering to a subject a therapeutically effective dosage of one TNF inhibitor, such as a specific TNF inhibitor, in combination with another TNF inhibitor, such as a non-specific TNF inhibitor.

Another preferred embodiment of the invention is a method for treatment of a nerve disorder in a subject comprising administering to a subject a therapeutically effective dosage of a TNF inhibitor in combination with a IL-1 inhibitor.

It is also an object of the invention to provide a novel pharmaceutical composition for treating nerve disorders in a subject comprising a therapeutically effective dosage of at least two substances selected from the group consisting of TNF inhibitors, IL-1 inhibitors, IL-6 inhibitors, IL-8 inhibitors, FAS inhibitors, FAS ligand inhibitors, and IFN-gamma inhibitors.

Nerve disorders treatable with the method and the pharmaceutical composition according to the invention are nerve disorders due to a reduced nerve reduction velocity, spinal disorders, nerve root injuries, nerve disorders caused by disc herniation, sciatica, cervical rhizopathy, low back pain, whiplash associated disorder, nerve disorders involving pain, nucleus pulposus-induced nerve injuries, and spinal cord compressions.

The subject which can be treated by these methods include any vertebrate, preferably mammals, and of those, most preferably humans.

Although a break-through in the treatment of spinal pain syndromes was made in 1997 when the involvement of pro-inflammatory cytokines, in particular TNF, became evident, the current invention offers an even more efficient way to treat i.a. sciatica and low back pain by pharmacological means. Since TNF acts synergistically with other pro-inflammatory cytokines inhibition of more cytokines than TNF is more efficient in acquiring the desired clinical effect.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE INVENTION

It has now surprisingly been shown possible to be able to treat nerve root injuries, or at least alleviate the symptoms of nerve root injuries by using a pharmaceutical composition comprising a therapeutically active amount of a TNF-alpha inhibitor. TNF-alpha inhibitors, include but are not limited to, metalloproteinase (MMP) inhibitors (excluding methylprednisolone), tetracyclines, chemically modified tetracyclines, quinolones, corticosteroids, thalidomide, lazaroids, pentoxifylline, hydroxamic acid derivatives, napthopyrans, soluble cytokine receptors, monoclonal antibodies towards TNF-alpha, amrinone, pimobendan, vesnarinone, phosphodiesterase inhibitors, lactoferrin and lactoferrin derived analogous, and melatonin in the form of bases or addition salts together with a pharmaceutically acceptable carrier.

By "therapeutically active amount" and "therapeutically effective dosage" are intended to be an amount that will lead to a desired therapeutic effect, i.e., an amount that will lead to an improvement of the patient's condition. In one preferred example, an amount sufficient to ameliorate or treat a condition associated with a nerve disorder.

By "mammal" is meant to include but is not limited to primate, human, canine, porcine, equine, murine, feline, caprine, ovine, bovine, lupine, camelid, cervidae, rodent, avian and ichthyes. By animal is meant to include any vertebrate animal wherein there is a potential for nerve root injury.

As used herein, the term "antibody" is meant to refer to complete, intact antibodies, and Fab fragments, scFv, and F(ab)$_2$ fragments thereof. Complete, intact antibodies include monoclonal antibodies such as murine monoclonal antibodies (mAb), chimeric antibodies, humanized antibodies and human. The production of antibodies and the protein structures of complete, intact antibodies, Fab fragments, scFv fragments and F(ab)$_2$ fragments and the organization of the genetic sequences that encode such molecules, are well known and are described, for example, in Harlow et al., ANTIBODIES: A LABORATORY MANUAL, Cold Spring Harbor Laboratory, Cold Spring Harbor, N.Y. (1988) and Harlow et al., USING ANTIBODIES: A LABORATORY MANUAL, Cold Spring Harbor Press, 1999, which are herein incorporated by reference in their entirety.

By "epitope" is meant a region on an antigen molecule to which an antibody or an immunogenic fragment thereof binds specifically. The epitope can be a three dimensional epitope formed from residues on different regions of a protein antigen molecule, which, in a naive state, are closely apposed due to protein folding. "Epitope" as used herein can also mean an epitope created by a peptide or hapten portion of TNF-alpha and not a three dimensional epitope. Preferred epitopes are those wherein when bound to an immunogen (antibody, antibody fragment, or immunogenic fusion protein) results in inhibited or blocked TNF-alpha activity.

By "TNF-alpha blocking" is meant a compound or composition that blocks, inhibits or prevents the activity of TNF or TNF-alpha.

Compounds that possess TNF-alpha inhibitory activity are for example tetracyclines, (e.g., tetracycline, doxycycline, lymecycline, oxytetracycline, minocycline), and chemically modified tetracyclines (e.g., dedimethylamino-tetracycline), hydroxamic acid compounds, carbocyclic acids and derivatives, thalidomide, lazaroids, pentoxifylline, napthopyrans, soluble cytokine receptors, monoclonal antibodies towards INF-alpha, amrinone, pimobendan, vesnarinone, phosphodiesterase inhibitors, lactoferrin and lactoferrin derived analogs, melatonin, norfloxacine, ofloxacine, ciprofloxacine, gatifloxacine, pefloxacine, lomefloxacine, temafloxacine, TTP and p38 kinase inhibitors. These compounds can be present as bases or in the form of addition salts, whichever possesses the best or preferred pharmaceutical effect, and best property to be brought into a suitable pharmaceutical composition. A more complete list is given below.

As stated above, there are several different types of cytokine blocking substances and pharmacological preparations that may be used according to the invention, and those substances may be grouped in different subclasses:

| TNF inhibitors | | | |
|---|---|---|---|
| Specific TNF inhibitors | | | |
| Monoclonal antibodies | such as: infliximab, CDP-571 (HUMICADE ™), D2E7 (Adalimumab), and CDP-870; | | |
| Polyclonal antibodies; Soluble cytokine receptors | such as: etanercept, lenercept, pegylated TNF receptor type I, and TBP-1; | | |
| TNF receptor antagonists; Antisense oligonucleotides; | such as: ISIS-104838 | | |
| Non-specific TNF inhibitors | | | |
| 5,6-dimethylxanthenone-4-acetic acid (acemannan); AGT-1; ANA 245; AWD 12281; BN 58705; Caspase inhibitors; CBP-1011; CC 1069; CC 1080; CDC 801; CDDO; CH-3697; CLX 1100; CM 101; CT3; CT 2576; CPH 82; CV 1013; Cyclosporin; Compounds used in anti-cancer treatment | such as: the binuclear DNA threading transition metal complexes and pharmaceutical compositions comprising them described in WO 99/15535, and methotrexate; | | |
| Declopramide; DPC 333; DWP 205297; DY 9973; Edodekin alfa Flt ligand (available from Immunex); Gallium nitrate; HP 228; Hydroxamic acid derivates; IL-12; IL-18; Ilodekacin; Ilomastat; ITF-2357; JTE 607; Lactoferrin; Lactoferrin derived or derivable peptides | such as: the peptides described in WO 00/01730; | | |
| Lazaroids; nonglucocorticoid 21-aminosteroids | such as: U-74389G (16-desmethyl tirilazad), and U-74500; | | |
| LPS agonist Esai; Melancortin agonists Mercaptoethylguanidine; Metoclopramide; MMP inhibitors (i.e. matrix metalloproteinase inhibitors or TACE inhibitors, i.e. TNF Alpha Converting Enzyme-inhibitors) | such as: HP-228; such as: Tetracyclines | | such as: Doxycycline, Lymecycline, Oxi-tetracycline, Tetracycline, and Minocycline; |
| | Synthetic tetracycline derivates (CMT = Chemically Modified Tetracyclines); KB-R7785; TIMP1 and TIMP2; adTIMP2 and adTIMP2; | | |
| M-PGA; Napthopyrans; NCS-700; Nimesulide; NR58-3.14.3; p38 kinase inhibitors | such as: VX-702, VX-740, VX-745 (Pralnacasan), VX-765, VX-850, SB-202190, SB-203580, and Pyridinyl imidazoles; | | |
| PCM-4; PD-168787; Pentoxifyllin derviates; Pharma projects no. 6181, 6019 and 4657; | such as: CC-1088, Ro 20-1724, rolipram, amrinone, | | |

| | | |
|---|---|---|
| Phosphodiesterase I, II, III, IV, and V-inhibitors | pimobendan, vesnarinone, and SB 207499; | |
| Piclamastat; PMS-601; Prostaglandins | such as: Iloprost (prostacyclin); | |
| Quinolones (chinolones) | such as: Norfloxacin, Levofloxacin, Enoxacin, Sparfloxacin, Temafloxacin, Moxifloxacin, Gatifloxacin, Gemifloxacin, Grepafloxacin, Trovafloxacin, Ofloxacin, Ciprofloxacin, Pefloxacin, Lomefloxacin, and Temafloxacin; | |
| RDP-58; RIP-3 Sch-23863; SH-636; Solimastat; SR-31747; Tasonermin; Thalidomide derivates (or SelCID = Selective Cytokin inhibitors, e.g. thalidomide derivate) TNF alpha proteinase inhibitor available from Immunex; TNF-484A; Tristetraproline (TTP) (available from AstraZeneca); VRCTC 310; Yissum project no. 11649; Zanamivir | such as: CC = 1088 CDC = 501, and CDC = 801; | |

Inhibitors of Interleukin-1 alpha and beta (IL-1α and IL-1β)

Specific inhibitors of IL-1α and IL-1β

| | | |
|---|---|---|
| Monoclonal antibodies | such as; CDP-484; | |
| Soluble cytokine receptors; IL-1 type II receptor (decoy RII); Receptor antagonists Antisense oligonucleotides Non-specific inhibitors of IL-1α and IL-1β | such as; IL-1ra, anakinra (KINERET ®), and ORTHOKIN ®; | |
| MMP inhibitors (i.e. matrix metalloproteinase inhibitors), | such as: | such as: Doxycycline, Trovafloxacin, Lymecycline, Oxitetra-cycline, Tetracycline, Minocycline, and synthetic tetracycline derivatives, such as CMT, i.e. Chemically Modified Tetracyclines; |
| | Prinomastat (AG3340); | |
| | Batimastat; Marimastat; BB-3644; KB-R7785; TIMP-1, and TIMP-2, adTIMP-1 (adenoviral delivery of TIMP-1), and adTIMP-2 (adenoviral delivery of TIMP-2); | |
| Quinolones (chinolones) | such as: Norfloxacin, Levofloxacin, Enoxacin, Sparfloxacin, Temafloxacin, Moxifloxacin, Gatifloxacin, Gemifloxacin, Grepafloxacin, Trovafloxacin, Ofloxacin, Ciprofloxacin, Pefloxacin, Lomefloxacin, Temafloxacin; | |
| Prostaglandins; Iloprost (prostacyclin); Phosphodiesterase I, II, III, IV, and V-inhibitors; CC-1088, Ro 20-1724, rolipram, amrinone, pimobendan, vesnarinone, SB 207499 | | |

Inhibitors of Interleukin-6 (IL-6)

Specific inhibitors of IL-6

Monoclonal antibodies; Soluble cytokine receptors; Receptor antagonists Antisense oligonucleotides Non-specific inhibitors of IL-6

| | | |
|---|---|---|
| MMP inhibitors (i.e. matrix metalloproteinase inhibitors) | such as: Tetracyclines | such as: Doxycycline, Lymecycline, Oxitetra-cycline, Tetracycline Minocycline, and synthetic tetracycline derivatives, such as CMT, i.e. Chemically Modified Tetracyclines; |
| | Prinomastat (AG3340); Batimastat; Marimastat; BB-3644; KB-R7785; TIMP-1, and TIMP-2, adTIMP-1 (adenoviral delivery of TIMP-1). and adTIMP-2 (adenoviral delivery of TIMP-2); | |

| | |
|---|---|
| Quinolones (chinolones) | such as: Norfloxacin, Levofloxacin, Enoxacin, Sparfloxacin, Temafloxacin, Moxifloxacin, Gatifloxacin, Gemifloxacin, Grepafloxacin, Trovafloxacin, Ofloxacin, Ciprofloxacin, Pefloxacin, Lomefloxacin, Temafloxacin; |

Prostaglandins;
Iloprost (prostacyclin);
Cyclosporin
Pentoxifyllin derivates;
Hydroxamic acid derivates;
Phosphodiesterase I, II, III, IV, and V-inhibitors;
CC-1088, Ro 20-1724, rolipram, amrinone, pimobendan, vesnarinone, SB 207499;
Melanin and melancortin agonists;
HP-228
Inhibitors of Interleukin-8 (IL-8)
Specific inhibitors of IL-8

Monoclonal antibodies;
Soluble cytokine receptors;
Receptor antagonists;
Antisense oligonucleotides;
Non-specific inhibitors of IL-8

| | | |
|---|---|---|
| Quinolones (chinolones) | such as: Norfloxacin, Levofloxacin, Enoxacin, Sparfloxacin, Temafloxacin, Moxifloxacin, Gatifloxacin, Gemifloxacin, Grepafloxacin, Trovafloxacin, Ofloxacin, Ciprofloxacin, Pefloxacin, Lomefloxacin, Temafloxacin; | |
| Thalidomide derivates | such as: SelCID, i.e. Selective Cytokine inhibitors | such as: CC-1088, CDC-501, CDC-801 and Linomide (Ro-quininex ®); |

Lazaroids;
Cyclosporin;
Pentoxifyllin derivates;

FAS Inhibitors

Specific FAS inhibitors

Monoclonal antibodies;
Soluble cytokine receptors;
Receptor antagonists;
Antisense oligonucleotides;
Non-specific FAS inhibitors Inhibitors of FAS ligands
Specific inhibitors of FAS ligands Monoclonal antibodies;
Soluble cytokine receptors;
Receptor antagonists;
Antisense oligonucleotides;
Non-specific inhibitors of FAS ligands Inhibitors of interferon-gamma (IFN-gamma)
Specific IFN-gamma inhibitors Monoclonal antibodies;
Soluble cytokine receptors;
Receptor antagonists;
Antisense oligonucleotides;
Non-specific IFN-gamma inhibitors

| | | |
|---|---|---|
| MMP inhibitors (i.e. matrix metalloproteinase inhibitors) | such as: Tetracyclines | such as: Doxycycline, Trovafloxacin, Lymecycline Oxitetracycline, Tetracycline, Minocycline, and synthetic tetracycline derivatives, such as CMT, i.e. Chemically Modified Tetracyclines; |
| | Prinomastat (AG3340); Batimastat; Marimastat; BB-3644; KB-R7785; TIMP-1, and TIMP-2, adTIMP-1 (adenoviral delivery of TIMP-1), and adTIMP-2 (adenoviral delivery of TIMP-2); | |
| Quinolones (chinolones) | such as: Norfloxacin, Levofloxacin, Enoxacin, Sparfloxacin, Temafloxacin, Moxifloxacin, Gatifloxacin, Gemifloxacin, Grepafloxacin, Trovafloxacin, Ofloxacin, Ciprofloxacin, Pefloxacin, Lomefloxacin, | |

-continued

Temafloxacin,
Rebamipide, and
Nalidixic acid;

Lazaroids:
Pentoxifyllin derivates;
Phosphodiesterase I, II,
III, IV, and V-inhibitors;
CC-1088, Ro 20-1724,
rolipram, amrinone,
pimobendan,
vesnarinone, SB
207499;

Also contemplated are the pharmaceutically acceptable bases and salts of the substances listed above.

Preferred groups of TNF-alpha blocking substances for use according to the present invention are soluble cytokine receptors, monoclonal antibodies, and tetracyclines or chemically modified tetracyclines.

Two preferred substances for use according to the present invention are the monoclonal antibodies, D2E7 and CDP-870.

D2E7 is a fully humanized monoclonal antibody directed against human TNF-alpha, which has been developed by Knoll and Cambridge Antibody Technology. A transgenic recombinant version of this antibody is under development by Genzyme Transgenic. The invention contemplates any antibody that binds to the same epitope as D2E7 or that has the same TNF-alpha inhibitory effect as D2E7. Preferably the antibody is primatized®, humanized or human.

CDP-870 (or CDP 870) is a humanized antibody fragment with high affinity to TNF-alpha. It has been developed by Celltech Group plc, and is co-developed with Pharmacia Corporation. The invention contemplates any antibody, antibody fragment or immunogen that binds to the same epitope as CDP-870 or that has the same TNF-alpha inhibitory activity as CDP-870. Preferably the antibody, antibody fragment or immunogen has the same or similar TNF-alpha inhibitory activity. Preferably the antibody, antibody fragment or immunogen is primatized, humanized or human.

According to a preferred embodiment, one of the substances used is a TNF inhibitor. According to a preferred variant of this embodiment the TNF inhibitor is a monoclonal antibody directed against TNF, such as infliximab, CDP-571, D2E7 or CDP-870. According to another preferred variant of this embodiment the TNF inhibitor used is a soluble cytokine TNF receptor, such as etanercept. According to another preferred variant of this embodiment the TNF inhibitor used is a binuclear DNA threading transition metal complex with anti-cancer effect. According to another preferred variant of this embodiment the TNF inhibitor used is a lactoferrin derivable peptide. According to another preferred variant of this embodiment the TNF inhibitor used is an MMP inhibitor, such as doxycycline. According to another preferred variant of this embodiment the TNF inhibitor used is a p38 kinase inhibitor. According to yet another preferred variant of this embodiment the substance used is TTP.

According to another preferred embodiment, one of the substances is a specific TNF inhibitor, such as infliximab, CDP-571, D2E7 or CDP-870, which is use in combination with a non-specific TNF inhibitor, such as doxycycline.

Doxycycline inhibits the action of TNF in a non-specific manner. TNF and other similar bioactive substances are first produced in an inactive form and transported to the cell membrane. Upon activation, the active part of the pro-TNF is cleaved and released. This process is called shedding and may be initiated by one or more enzymes. These enzymes have in common that they are metalloproteinases, i.e. dependent of a metal-ion for their function. Doxycycline and other tetracyclines are known to bind to metal-ions and will thereby inhibit the action of metalloproteinases and subsequently the release of TNF and other pro-inflammatory cytokines in a non-specific manner. A monoclonal anti-TNF antibody, on the other hand, will bind directly to TNF and thereby inhibit TNF in a more specific way than doxycycline. The inhibition may thus be assumed to be more efficient but will be restricted to TNF. However, in the work leading to the present invention, it was found that anti-TNF treatment was more efficient than doxycycline treatment. However, the most efficient way to inhibit the nucleus pulpous induced reduction in nerve root conduction velocity was found to be to combine a TNF-inhibitor and an IL-1 inhibitor. TNF is known to be orchestrating much of the inflammatory events. Except for having direct effects on target-receptors, it may also act through other cytokines by stimulation of their release. Although one may assume that specific inhibition may block both the direct effects of TNF and its stimulatory effects on other cytokines, the work leading to the present invention showed that it is possible to further inhibit the action of TNF by inhibiting cytokines that are produced and released by TNF stimulation. In addition to inhibiting the stimulatory effects of TNF, one thereby also inhibits the effects of these synergistic cytokines downstream. Since these synergistic cytokines may also induce release and production of TNF, the inhibition of these cytokines also reduces the level of TNF. According to the present invention it is shown that the use of also one or more inhibitors of other cytokines is more efficient in blocking the nucleus pulposus induced effects on adjacent nerve roots.

The combination of inhibitors of one specific cytokine with different mechanisms is also shown to be more efficient than the use of a single inhibitor. For instance, TNF may be inhibited at the synthesis-level (e.g., by pentoxifylline), at translation by anti-sense (e.g., by ISIS-104838), at shedding (e.g., by doxycycline), and later by antibodies (e.g., by infliximab or CDP-870) or soluble receptors (e.g., by etanercept or lenercept). Thus, there are at least five mechanisms useful for inhibiting TNF. The combination of two or more drugs that act through different mechanisms therefore induces a more efficient inhibition of that certain cytokine than the use of one single drug. A special benefit is achieved if a specific inhibitor or a key substance, for instance a monoclonal antibody against TNF, and a non-specific inhibitor that also blocks other cytokines, for instance doxycycline. This combination achieves inhibition of TNF at two levels (shedding and binding of active TNF) as well as inhibition of other synergistic cytokines.

According to another preferred embodiment one of the substances used is an IL-1 inhibitor.

According to an especially preferred embodiment one of the substances used is a TNF inhibitor and one is an IL-1 inhibitor.

Said at least two substances are preferably administered simultaneously, but they may also be administered separately.

The substances according to the invention may also be administered in combination with other drugs or compounds, provided that these other drugs or compounds do not eliminate the desired effects according to the present invention, i.e., the effect on TNF-alpha.

The invention further relates to a method for inhibiting the symptoms of nerve root injury.

The effects of doxycycline, soluble cytokine-receptors, and monoclonal cytokine-antibodies have been studied and representative methods used and results obtained are disclosed below. Although the present invention has been described in detail with reference to examples herein, it is understood that various modifications can be made without departing from the spirit of the invention, and would be readily known to the skilled artisan.

The compounds of the invention can be administered in a variety of dosage forms, e.g., orally (per os), in the form of tablets, capsules, sugar or film coated tablets, liquid solutions; rectally, in the form of suppositories; parenterally, e.g., intramuscularly (i.m.), subcutaneous (s.c.), intracerebroventricular (i.c.v.), intrathecal (i.t.), epidurally, transepidermally or by intravenous (i.v.) injection or infusion; by inhalation; or intranasally.

The therapeutic regimen for the different clinical syndromes may be adapted to the disease or condition, medical history of the subject as would be know to the skilled artisan or clinician. Factors to be considered but not limiting to the route of administration, the form in which the compound is administered, the age, weight, sex, and condition of the subject involved.

For example, the oral route is employed, in general, for all conditions, requiring such compounds. In emergency cases, preference is sometimes given to intravenous injection. For these purposes, the compounds of the invention can be administered, for example, orally at doses ranging from about 20 to about 1500 mg/day. Of course, these dosage regimens may be adjusted to provide the optimal therapeutic response depending on the subject's condition.

The nature of the pharmaceutical composition containing the compounds of the invention in association with pharmaceutically acceptable carriers or diluents will, of course, depend upon the desired route of administration. The composition may be formulated in the conventional manner with the usual ingredients. For example, the compounds of the invention may be administered in the form of aqueous or oily solutions or suspensions, tablets, pills, gelatin capsules (hard or soft ones), syrups, drops or suppositories.

For oral administration, the pharmaceutical compositions containing the compounds of the invention are preferably tablets, pills or gelatine capsules, which contain the active substance or substances together with diluents, such as lactose, dextrose, sucrose, mannitol, sorbitol, cellulose; lubricants, e.g., silica, talc, stearic acid, magnesium or calcium stearate, and/or polyethylene glycols; or they may also contain binders, such as starches, gelatine, methyl cellulose, carboxymethylcellulose, gum arabic, tragacanth, polyvinylpyrrolidone; disaggregating agents such as starches, alginic acid, alginates, sodium starch glycolate, microcrystalline cellulose; effervescing agents, such a carbonates and acids; dyestuffs; sweeteners; wetting agents, such as lecithin, polysorbates, laurylsulphates; and in general non-toxic and pharmaceutically inert substances used in the formulation of pharmaceutical compositions. Said pharmaceutical compositions may be manufactured in known manners, e.g., by means of mixing, granulating, tableting, sugar-coating or film-coating processes. Film providing compounds can be selected to provide release in the right place or at the appropriate time in the intestinal tract with regard to absorption and maximum effect. Thus pH-dependent film formers can be used to allow absorption in the intestines as such, whereby different phthalates are normally used or acrylic acid/methacrylic acid derivatives and polymers.

The liquid dispersions for oral administration may be, e.g., syrups, emulsions, and suspensions.

The syrups may contain as carrier, e.g., saccharose, or saccharose with glycerine and/or mannitol and/or sorbitol.

Suspensions and emulsions may contain as Garner, e.g., a natural gum, such as gum arabic, xanthan gum, agar, sodium alginate, pectin, methyl cellulose, carboxymethylcellulose, polyvinyl alcohol.

The suspension or solutions for intramuscular injections may contain together with the active compound, a pharmaceutically acceptable carrier, such as e.g., sterile water, olive oil (or other vegetable or nut derived oil), ethyl oleate, glycols", e.g., propylene glycol, and if so desired, a suitable amount of lidocaine hydrochloride. Adjuvants for triggering the injection effect can be added as well.

The solutions for intravenous injection or infusion may contain as carrier, e.g., sterile water, or preferably, a sterile isotonic saline solution, as well as adjuvants used in the field of injection of active compounds. Such solutions would also be suitable for i.m. and i.c.v. injection.

The suppositories may contain together with the active compounds, a pharmaceutically acceptable carrier, e.g., cocoa-butter polyethylene glycol, a polyethylene sorbitan fatty acid ester surfactant or lecithin.

Examples of suitable doses of the active agents contemplated for different administration routes are given below.

1 Per os 10-300 mg i.m. 25-100 mg i.v. 2.5-25 mg i.t. 0.1-25 mg (daily—every 3.sup.rd month) inhalation 0.2-40 mg transepidermally 10-100 mg intranasally 0.1- 10 mg s.c. 5-10 mg i.c.v. 0.1-25 mg (daily—every 3.sup.rd month) epidurally 1-100 mg These ranges are approximate (e.g., about 1 to about 100) and may vary depending on the specific agent being administered and the nature of the disorder in the subject. Thus, it is further contemplated that any dosage in between for the cited ranges may also be used.

Examples of suitable doses for different TNF-alpha inhibitors are given in the table below.

Preferred Dosage of TNF-Alpha Blocking Substance and Administration Route

Lenercept i.v. 5-200 10-100 30-80 (all given in mg for administration once every 4th week)

TBP-1 i.v. 5-200 10-100 30-80 (all given in mg for administration once every 4th week) CDP-571 (HUMICADE) i.v. 1-100 5-10 5-10 (all given in mg/kg body weight for administration as a single dose)

D2E7 i.v. 0.1-50 0.5-10 1-10 s.c. 0.1-50 0.5-10 1-10 (all given in mg/kg body weight for administration as a single dose)

Iloprost i.v. 0.1-2000 1-1500 100-1000 (all given in ug/kg body weight/day) intranasally 50-250 100-150 100-150 (all given in ug/day)

Thalidomide 100-1200 300-1000 500-800 (all given in ug/day) CC-1 088 Per os 50-1200 200-800 400-600 (all given in mg/day)

CDP-870 i.v. 1-50 2-10 3-8 (all given in mg/kg body weight for administration once every 4th week)

HP-228 i.v. 5-100 10-50 20-40 (all given in .mu.g/kg body weight)

ISIS-10483 Per os 1-100 10-50 20-50 s.c. 1-100 10-50 20-50 i.v. 1-100 10-50 20-50 (all given in mg)

ARIFLO (SB 207499 Per os 10-100 30-60 30-45 (all given in mg/day)

KB-R7785 s.c. 100-500 100-300 150-250 (all given in mg/kg body weight/day)

CDC-501 Per os 50-1200 200-800 400-600 (all given in mg/day)

CDC-801 (ROQUININEX) Per os 50-1200 200-800 400-600 (all given in mg/day)

Prinomastat, Batimastat, and Marimastat Per os 1-250 mg 5-100 mg 10-50 mg (all given in mg twice/day)

Linomide Per os 0.1-25 5-20 110-15 (all given in mg/kg body weight/day)

IL-1 blocking substance and administration route

Anakinra (KINERET®) s.c. 10-200 50-150 100 (all given in mg/day)

Incorporation by Reference and Examples

Although the present invention has been described in detail with reference to examples below, it is understood that various modifications can be made without departing from the spirit of the invention, and would be readily known to the skilled artisan. All cited patents and publications referred to in this application are herein incorporated by reference in their entirety for all purposes.

The application incorporates herein by reference in their entirety International Application No. PCT/SE99/01670 and Swedish Application Nos. 9803276-6 and 9803710-4 for all purposes.

EXAMPLES

Example 1

Study Design

The effects of nucleus pulposus and various treatments to block TNF-activity were evaluated in an experimental set-up using immunohistochemistry and nerve conduction velocity recordings.

Summary of Background Data

A meta-analysis of observed effects induced by nucleus pulposus reveals that these effects might relate to one specific cytokine, Tumor Necrosis Factor alpha (TNF-alpha).

Objectives

To assess the presence of TNF-alpha in pig nucleus pulposus cells and to see if blockage of TNF-alpha also blocks the nucleus pulposus-induced reduction of nerve root conduction velocity.

Methods

Series-1: Cultured nucleus pulposus-cells were immunohistologically stained with a monoclonal antibody for TNF-alpha.

Series-2: Nucleus pulposus was harvested from lumbar discs and applied to the sacrococcygeal cauda equina in 13 pigs autologously. Four pigs received 100 mg of doxycycline intravenously, 8 pigs had a blocking monoclonal antibody to TNF-alpha applied locally in the nucleus pulposus, and 4 pigs remained non-treated (controls). Three days after the application the nerve root conduction velocity was determined over the application zone by local electrical stimulation.

Series-3: Thirteen pigs had autologous nucleus pulposus placed onto their sacrococcygeal cauda equina similar to series-2. Five pigs (body weight 25 kg) received REMICADE® (infliximab) 100 mg i.v. preoperatively, and 8 pigs received ENBREL® (etanercept) 12.5 mg s.c. preoperatively and additionally 12.5 mg s.c. three days after the operation. Seven days after the nucleus pulposus-application the nerve root conduction velocity was determined over the application zone by local electrical stimulation according to series-2.

Results

Series-1: TNF-alpha was found to be present in the nucleus pulposus-cells.

Series-2: The selective antibody to TNF-alpha limited the reduction of nerve conduction velocity. However, treatment with doxycycline significantly blocked the nucleus pulposus-induced reduction of conduction velocity.

Series-3: Both drugs (infliximab, and etanercept) blocked the nucleus pulposus induced nerve injury efficiently. Normal average nerve conduction velocities were found after 15 treatment with both of these two drugs.

Conclusion

For the first time a specific substance, Tumor Necrosis Factor-alpha (TNF.alpha.), has been linked to the nucleus pulposus-induced effects of nerve roots after local application. Although the effects of this substance may be synergistic with other similar substances, the data of the present study may be of significant importance for the continued understanding of nucleus pulposus' biologic activity, and might also be of potential use for future treatment strategies of sciatica and other nerve root injury conditions or related conditions.

After previously being considered as just a biologically inactive tissue component compressing the spinal nerve root at disc herniation, the nucleus pulposus has recently been found to be highly active, inducing both structural and functional changes in adjacent nerve roots when applied epidurally (Kayama S, Konno S, Olmarker K, Yabuki S, Kikuchi S, Incision of the anulus fibrosis induces nerve root morphologic, vascular, and functional changes. An experimental study, Spine 1996; 21: 2539-43; Olmarker K, Brisby H, Yabuki S, Nordborg C, Rydevik B, The effects of normal, frozen, and hyaluronidase-digested nucleus pulposus on nerve root structure and function, Spine 1997; 22: 4715; discussion 476; Olmarker K, Byrod G, Comefjord M, Nordborg C, Rydevik B, Effects of methylprednisolone on nucleus pulposus-induced nerve root injury, Spine 1994; 19: 1803-8; Olmarker K, Nordborg C, Larsson K, Rydevik B, Ultrastructural changes in spinal nerve roots induced by autologous nucleus pulposus, Spine 1996; 21: 411-4; Olmarker K, Rydevik B, Nordborg C, Autologous nucleus pulposus induces neurophysiologic and histologic changes in porcine cauda equina nerve roots, Spine 1993; 18: 1425-32). It has thereby been established that autologous nucleus pulposus may induce axonal changes and a characteristic myelin injury (Kayama S, Konno S, Olmarker K, Yabuki S, Kikuchi S, Incision of the anulus fibrosis induces nerve root morphologic, vascular, and functional changes. An experimental study, Spine 1996; 21: 2539-43; Olmarker K, Byrod G, Comefjord M, Nordborg C, Rydevik B, Effects of methylprednisolone on nucleus pulposus-induced nerve root injury, Spine 1994; 19: 1803-8; Olmarker K, Nordborg C, Larsson K, Rydevik B, Ultrastructural changes in spinal nerve roots induced by autologous nucleus pulposus, Spine 1996; 21: 411-4; Olmarker K, Rydevik B, Nordborg C, Autologous nucleus pulposus induces neurophysiologic and histologic changes in porcine cauda equina nerve roots, Spine 1993; 18: 1425-32.), increased vascular permeability (Byrod G, Otani K, Brisby H, Rydevik B, Olmarker K, Methylprednisolone reduces the early vascular permeability increase in spinal nerve roots induced by epidural nucleus pulposus application, J Orthop Res 1987; 18: 6: 983-7), infra vascular coagulation (Kayama S, Konno S, Olmarker K, Yabuki S, Kikuchi S, Incision of the anulus fibrosis induces nerve root morphologic, vascular, and functional changes. An experimental study, Spine 1996; 21: 2539-43; Olmarker K, Blomquist J, Stromberg J, Nanmnark, U, Thomsen P, Rydevik B, Inflammatogenic properties of nucleus pulposus, Spine 1995; 20: 665-9.), and that membrane-bound structure or substances of the nucleus pulposus-cells are responsible for these effects (Kayama S, Konno S, Olmarker K, Yabuki S, Kikuchi S, Incision of the anulus fibrosis induces nerve root morphologic, vascular, and functional changes. An experimental study, Spine 1996; 21: 2539-43; Olmarker K, Brisby H, Yabuki S, Nordborg C, Rydevik B, The effects of normal, frozen, and hyaluronidase-digested nucleus pulposus on nerve root structure and function, Spine 1997; 22: 4715; discussion 476.). The effects have also been found to be efficiently blocked by methylprednisolone and cyclosporin A (Arai I, Konno S, Otani K, Kikuchi S, Olmarker K, Cyclosporin A blocks the toxic effects of nucleus pulposus on spinal nerve roots, Submitted; Olmarker K, Byrod G, Comefjord M, Nordborg C, Rydevik B, Effects of methylprednisolone on nucleus pulposus-induced nerve root injury, Spine 1994; 19: 1803-8.). When critically looking at these data, one realizes that there is at least one cytokine that relates to all of these effects, TNF-alpha.

To assess if TNF-alpha may be involved in the nucleus pulposus induced nerve root injury, the presence of TNF-alpha in nucleus pulposus-cells was assessed and was studied if the nucleus pulposus-induced effects could be blocked by doxycycline, a soluble TNF-receptor, and a selective monoclonal TNF-alpha antibody, the latter administered both locally in the nucleus pulposus and systemically.

Example 2

Material and Methods

Series-1, Presence of TNF-alpha in pig nucleus pulposus-cells:

Nucleus pulposus (NP) from a total of 13 lumbar and thoracic discs were obtained from 10 pigs, which were used for other purposes. NP was washed once in Ham's F 12 medium (Gibco BRL, Paisley, Scotland) and then centrifuged and suspended in 5 ml of collagenase solution in Ham's F12 medium (0.8 mg/ml, Sigma Chemical Co., St Louis, Mo., USA) for 40 minutes, at 37.degree. C. in 25 cm tissue culture flasks. The separated NP-cell pellets were suspended in DMEM/F12 1:1 medium (Gibco BRL, Paisley, Scotland) supplemented with 1% L-glutamine 200 mM (Gibco BRL, Paisley, Scotland), 50 mg/ml gentamycine sulphate (Gibco BRL, Paisley, Scotland) and 10% fetal calf serum (FCS), (Gibco BRL, Paisley, Scotland). The cells were cultured at 37.degree. C. and 5% $CO_2$ in air for 3-4 weeks and then cultured directly on tissue culture treated glass slides (Becton Dickinson & Co Labware, Franklin Lakes, N.J., USA). After 5 days on the glass slides, the cells were fixed in situ by exposing the slides to acetone for 10 minutes. After blocking irrelevant antigens by application of 3% $H_2O_2$ (Sigma Chemical Co., St Louis, Mo., USA) for 30 minutes and Horse Serum (ImmunoPure ABC, peroxidase mouse IgG staining kit nr.32028, Pierce, Rockford, Ill.) for 20 minutes, the primary antibody (Anti-pig TNF-alpha monoclonal purified antibody, Endogen, Cambridge, Mass., USA, Ordering Code MP-390) was applied over night at +40.degree C., diluted at 1: 10, 1:20 and 1:40 dilutions. For control, BSA (bovine serum albumin, Intergen Co, New York, USA) suspended in PBS (phosphate buffered saline, Merck, Darmstadt, Germany) was applied in the same fashion. The next day the cells were washed with 1% BSA in PBS and the secondary antibody (ImmunoPure ABC, peroxidase mouse IgG staining kit Cat. Cat. #32028, Pierce, Rockford, Ill.) was applied for 30 minutes. To enhance this reaction, the cells were exposed to Avidin-Biotin complex for an additional 30 minutes (ImmunoPure ABC, peroxidase mouse IgG staining kit Cat. #32028, Pierce, Rockford, Ill.). The cells were then exposed to 20 mg of DAB (3,3-diaminobenzidine tetrahydrochloride No. D-5905, Sigma Chemical Co., St Louis, Mo., USA) and 0.033 ml of 3% $H_2O_2$ in 10 ml of saline for 10 minutes. The cells were washed in PBS, dehydrated in a series of ethanol, mounted and examined by light microscopy by an unbiased observer for the presence of a brown coloration indicating the presence of TNF-alpha.

Series-2, Neurophysiologic evaluation:

Thirteen pigs (body weight 25-30 kg) received an intramuscular injection of 20 mg/kg body weight of KETALAR™ (ketamine, 50 mg/ml, Parke-Davis, Moms Plains, N.J.) and an intravenous injection of 4 mg/kg body weight of HYPNODIL® (methomidate chloride, 50 mg/ml, AB Leo, Helsingborg, Sweden) and 0.1 mg/kg body weight of STRESNIL® (azaperon, 2 mg/ml, Janssen Pharmaceutica, Beerse, Belgium). Anesthesia was maintained by additional intravenous injections of 2 mg/kg body weight of HYPNODIL® and 0.05 mg/kg body weight of STRESNIL®. The pigs also received an intravenous injection of 0.1 mg/kg of STESOLID NOVUM® (Diazepam, Dumex, Helsingborg, Sweden) after surgery.

Nucleus pulposus was harvested from the 5.sup.th lumbar disc through a retro peritoneal approach (Olmarker K, Rydevik B, Nordborg C, Autologous nucleus pulposus induces neurophysiologic and histologic changes in porcine cauda equina nerve roots, Spine 1993; 18:1425-32.). Approximately 40 mg of the nucleus pulposus was applied to the sacrococcygeal cauda equina through a midline incision and laminectomy of the first coccygeal vertebra. Four pigs did not receive any treatment (no treatment). Four other pigs received an intravenous infusion of 100 mg of doxycycline (Vibramycino, Pfizer Inc., New York, USA) in 100 ml of saline over 1 hour. In 5 pigs, the nucleus pulposus was mixed with 100 ul of a 1.11 mg/mL suspension of the anti-TNF-alpha antibody used in series 1, before application.

Three days after the application, the pigs were re-anesthetized by an intramuscular injection of 20 mg/kg body weight of KETALAR® and an intravenous injection of 35 mg/kg body weight 25 of PENTOTHAL® (Thiopental sodium, Abbott lab, Chicago, Ill.). The pigs were ventilated on a respirator. Anesthesia was maintained by an intravenous bolus injection of 100 mg/kg body weight of Chloralose ((a)-D(+)-gluco-chloralose, Merck, Darmstadt, Germany) and by a continuous supply of 30 mg/kg/hour of Chloralose. A laminectomy from the 4.sup.th sacral to the 3.sup.rd coccygeal vertebra was performed. The nerve roots were covered with SPONGOSTANE® (Ferrosan, Denmark). Local tissue temperature was continuously monitored and maintained at 37.5-38.0.degree. C. by means of a heating lamp.

The cauda equina was stimulated by two E2 subdermal platinum needle electrodes (Grass Instrument Co., Quincy, Mass.) which were connected to a Grass SD9 stimulator (Grass Instrument Co., Quincy, Mass.) and gently placed intermittently on the cauda equina first 10 mm cranial and then 10 mm caudal to the exposed area. To ensure that only impulses from exposed nerve fibers were registered, the nerve root that exited from the spinal canal between the two stimulation sites were cut. An electromyogram (EMG) was registered by two subdermal platinum needle electrodes which were placed into the paraspinal muscles in the tail approximately 10 mm apart. This procedure is reproducible and represents a functional measurement of the motor nerve fibers of the cauda equina nerve roots. The EMG was visualized using a Macintosh IIci computer provided with Superscope software and MacAdios II AID converter (GW Instruments, Sommerville, Mass.) together with a Grass P18 preamplifier (Grass Instrument Co., Quincy, Mass.). The separation distance between the first peaks of the EMG from the two recordings was determined, and the separation distance between the two stimulation sites on the cauda equina was measured with calipers. The nerve conduction velocity between the two stimulation sites could thus be calculated from these two measurements.

The person performing the neurophysiologic analyses was unaware of the experimental protocol for the individual animal. After finishing the complete study, the data were arranged in the three experimental groups and statistical differences between the groups were assessed by Student's t-test. The experimental protocol for this experiment was approved by the local animal research ethics committee.

Series-3:

Thirteen pigs had autologous nucleus pulposus placed onto their sacrococcygeal cauda equina similar to series-2. Five pigs (bodyweight 25 kg) received the human/murine monoclonal antibody, REMICADE® (infliximab, Immunex Corporation, Seattle, Wash. 98101, USA) 100 mg i.v. preoperatively, and 8 pigs received ENBREL® (etanercept, Centocor B. V., Leiden, the Netherlands) 12.5 mg s.c. preoperatively and additionally 12.5 mg s.c. three days after the operation. Seven days after the nucleus pulposus-application the nerve root conduction velocity was determined over the application zone by local electrical stimulation according to series-2. To blind the study, the neurophysiological evaluation was conducted in parallel to another study and the person performing the analyses did not know from which study and what treatment each specific animal was subjected to. No non-treated animals were included in the series-3 due to the pre-existing knowledge of nerve conduction velocity after seven days of either nucleus pulposus or fat (control) application. The statistical difference between the groups, infliximab, and etanercept, nucleus pulposus without treatment (positive control from previous data) and application of retroperitoneal fat (negative control from previous data) was assessed by using ANOVA and Fisher's PLSD at 5%.

Results

Series-1, Presence of TNF-alpha in pig nucleus pulposus-cells:

Examples of the light microscopic appearance of the stained glass slides. In the sections using BSA in PBS as "primary antibody" (control), no staining was observed, ensuring that there was no labeling and visualization of irrelevant antigens. When the anti-TNF-alpha antibody was applied at 1:40 dilution there was only weak staining. However, the staining increased with diminishing dilutions of the antibody. The staining was seen in the soma of the cells, and it was not possible to differentiate whether TNF-alpha was located in the cytoplasm, on the cell surface bound to the cell-membrane, or both.

Series-2 Neurophysiologic evaluation:

Application of non-modified nucleus pulposus and without any treatment induced a reduction in nerve conduction velocity similar to previous studies (Table 1). In contrast, treatment with doxycycline completely blocked this reduction ($p<0.01$ Student's t-test). Local application of anti-TNF-alpha-antibody also induced a partial block of this reduction, although not as complete as doxycycline and was not statistically significant as compared to the no treatment-series.

Series-3:

Treatment with both drugs seemed to prevent the nucleus pulposus-induced reduction of nerve root conduction velocities, since the average nerve conduction velocity for both these treatment groups were close to the average conduction of the fat-application series, as seen in a previous study (Table 2). The average nerve conduction velocity in pigs treated with ENBREL™ was statistically different from the average nerve conduction velocity in the series with pigs with no treatment. The average new conduction velocity in the group treated with REMICADE™ was also statistically significantly different from the average nerve conduction velocity in the group with no treatment.

TABLE 1

| | Series 2 | |
| --- | --- | --- |
| Treatment | n | NCV (m/s +/− SD) |
| Local anti-TNF alpha | 5 | 64 +/− 28 |
| Doxycycline | 4 | 76 +/− 9 |
| No treatment | 4 | 46 +/− 12 |

TABLE 2

| | Series 3 | |
| --- | --- | --- |
| Treatment | n | NCV (m/s +/− SD) |
| Fat* | 5 | 76 +/− 11 |
| ENBREL ® | 8 | 78 +/− 14 |
| REMICADE ® | 5 | 79 +/− 15 |
| No treatment | 5 | 45 +/− 19 |

Data included from Olmarker K, Rydevik B, Nordborg C, Autologous nucleus pulposus induces neurophysiologic and histologic changes in porcine cauda equina nerve roots, Spine 1993; 18:1425-32.

Discussion

The data of the present study demonstrated that TNF-alpha may be found in nucleus pulposus-cells of the pig. If TNF-alpha was blocked by a locally applied selective monoclonal antibody, the nucleus pulposus-induced reduction of nerve root conduction velocity was partially blocked, although not statistically significant as compared to the series with non-treated animals. However, if animals were treated systemically with doxycycline, infliximab, and etanercept to inhibit TNF-alpha, the reduction of nerve conduction velocity was significantly prevented.

In recent years, it has been verified that local application of autologous nucleus pulposus may injure the adjacent nerve roots. Thus, it has become evident that the nerve root injury seen as disc herniation may not be solely based on mechanical deformation of the nerve root, but may also be induced by unknown "biochemical effects" related to the epidural presence of herniated nucleus pulposus. Although this new research field has generated many experimental studies, the mechanisms and substances involved are not fully known. It has been seen that local application of autologous nucleus pulposus may induce axonal injury (Kayama S, Konno S, Olmarker K, Yabuki S, Kikuchi S, Incision of the anulus fibrosis induces nerve root morphologic, vascular, and functional changes. An experimental study, Spine 1996; 21: 2539-43; Olmarker K, Brisby H, Yabuki S, Nordborg C, Rydevik B, The effects of normal, frozen, and hyaluronidase-digested nucleus pulposus on nerve root structure and function, Spine 1997; 22: 4715; discussion 476; Olmarker K, Byrod G, Comefjord M, Nordborg C, Rydevik B, Effects of methylprednisolone on nucleus pulposus-induced nerve root injury, Spine 1994; 19: 1803-8; Olmarker K, Myers R R, Pathogenesis of sciatic pain: Role of herniated nucleus pulposus and deformation of spinal nerve root and DRG, Pain, 1998, 78: 9-105; Olmarker K, Nordborg C, Larsson K, Rydevik B, Ultrastructural changes in spinal nerve roots induced by autologous nucleus pulposus, Spine 1996; 21: 411-4; Olmarker K, Rydevik B, Nordborg C, Autologous nucleus pulposus induces neurophysiologic and histologic changes in porcine cauda equina nerve roots, Spine 1993; 18: 1425-32), a characteristic injury of the myelin sheath (Kayama S, Konno S, Olmarker K, Yabuki S, Kikuchi S, Incision of the anulus fibrosis induces nerve root morphologic, vascular, and functional changes. An experimental study, Spine 1996; 21: 2539-43; Olmarker K, Byrod G, Comefjord M, Nordborg C, Rydevik B, Effects of methylprednisolone on nucleus pulposus-induced nerve root injury, Spine 1994; 19: 1803-8; Olmarker K, Myers R R, Pathogenesis of sciatic pain: Role of herniated nucleus pulposus and deformation of spinal nerve root and DRG, Pain, 1998, 78: 9-105; Olmarker K, Nordborg C, Larsson K, Rydevik B, Ultrastructural changes in spinal nerve roots induced by autologous nucleus pulposus, Spine 1996; 21: 411-4; Olmarker K, Rydevik B, Nordborg C, Autologous nucleus pulposus induces neurophysiologic and histologic changes in porcine cauda equina nerve roots, Spine 1993; 18: 1425-32), a local increase of vascular permeability (Byrod G, Otani K, Brisby H, Rydevik B, Olmarker K, Methylprednisolone reduces the early vascular permeability increase in spinal nerve roots induced by epidural nucleus pulposus application, J. Orthop. Res. 1987; 186: 983-7; Olmarker K, Blomquist J, Stromberg J, Nanmnark, U, Thomsen P, Rydevik B, Inflammatogenic properties of nucleus pulposus, Spine 1995; 20: 665-9) infra vascular coagulations, reduction of infra neural blood flow (Otani K, Arai I, Mao G P, Konno S, Olmarker K, Kikuchi S, Nucleus pulposus-induced nerve root injury. The relationship between blood flow and nerve conduction velocity, Neurosurgery 1999; 45: 619-20), and leukotaxis (Olmarker K, Blomquist J, Stromberg J, Namnnark, U, Thomsen P, Rydevik B, Inflanimatogenic properties of nucleus pulposus, Spine 1995; 20: 665-9). It has been seen that the nucleus pulposus-related effects may be blocked efficiently by methylprednisolone (Olmarker K, Byrod G, Comefjord M, Nordborg C, Rydevik B, Effects of methylprednisolone on nucleus pulposus-induced nerve root injury, Spine 1994; 19: 1803-8) and cyclosporin A (Arai I, Konno S, Otani K, Kikuchi S, Olmarker K, Cyclosporin A blocks the toxic effects of nucleus pulposus on spinal nerve roots, Submitted, and slightly less efficiently by indomethacin (Arai I, Mao G P, Otani K, Komo S, Kikuchi S, Olmarker K, Indomethacin blocks nucleus pulposus related effects in adjacent nerve roots, Accepted for publication in Eura Spine J.), and lidocaine (Yabuki S, Kawaguchi Y, Olmarker K, Rydevik B, Effects of lidocaine on nucleus pulposus-induced nerve root injury, Spine, 1998; 23: 29: 2383-89). Further, it has been understood that the effects are mediated by the nucleus pulposus-cells (37), particularly by substances or structures bound to the cell-membranes (Kayama S, Olmarker K, Larsson K, Sjoren-Jansson E, Lindahl A, Rydevik D, Cultured, autologous nucleus pulposus cells induce structural and functional changes in spinal nerve roots, Spine, 1998; 23: 2155-8). When critically considering these data, it becomes evident that at least one specific cytokine could be related to these observed effects, Tumor Necrosis Factor-alpha (TNF-alpha). TNF-alpha may induce nerve injury (Liberski P P, Yanagihara R, Nerurkar V, Gajdusek D C, Further ultrastructural studies of lesions induced in the optic nerve by tumor necrosis factor alpha (TNF-alpha): a comparison with experimental Creutzfeldt-Jakob disease, Acta Neurobiol En (Warsz) 1994; 54: 209-18; Madigan M C, Sadun A A, Rao N S, Dugel P U, Tenhula W N, Gill P S, Tumor necrosis factor-alpha (TNF-alpha)-induced optic neuropathy in rabbits, Neurol Res 1996; 18: 176-84; Petrovich M S, Hsu H Y, Gu X, Dugal P, Heller K B, Sadun A A, Pentoxifylline suppression of TNF-alpha mediated axonal degeneration in the rabbit optic nerve, Neurol Res 1997; 19: 551-4; Said G, Hontebeyrie-Joskowicz M, Nerve lesions induced by macrophage activation, Res Immunol 1992; 143: 589-99; Wagner R, Myers R R, Endoneurial injection of TNF-alpha produces neuropathic pain behaviours, Neuroreport 1996; 7: 2897-901), mainly seen as a characteristic myelin injury that closely resembles the nucleus pulposus-induced myelin-injury (Liberski P P, Yanagihara R, Nerurkar V, Gajdusek D C, Further ultrastructural studies of lesions induced in the optic nerve by tumor necrosis factor alpha (TNF-alpha): a comparison with experimental Creutzfeldt-Jakob disease, Acta Neurobiol En (Warsz) 1994; 54: 209-18; Redford E J, Hall S M, Smith K J, Vascular changes and demyelination induced by the intraneural injection of tumour necrosis factor, Brain 1995; 118: 869-78; Sehnaj K W, Raine C S, Tumor necrosis factor mediates myelin and oligodendrocytc damage in vitro, Ann Neurol 1988; 23: 339-46; Sharief M K, Ingram D A, Swash M, Circulating tumor necrosis factor-alpha correlates with electrodiagnostic abnormalities in Guillain-Barre syndrome, Ann Neurol 1997; 42: 6873; Tsukamoto T, Ishikawa M, Yamamoto T, Suppressive effects of TNF-alpha on myclin formation in vitro, Acta Neurol Scand 1995; 91: 71-5; Villarroya H, Violleau K, Ben Younes-Chennoufi A, Baumann N, Myelin-induced experimental allergic encephalomyelitis in Lewis rats: tumor necrosis factor alpha levels in serum of cerebrospinal fluid immunohistochemical expression in glial cells and neurophages of optic nerve and spinal cord, J Neuroimmunol 1996; 64: 55-61; Wagner R, Myers R R, Endoneurial injection of TNF-alpha produces neuropathic pain behaviours, Neuroreport 1996; 7: 2897-901; Zhu J, Bai X F, Mix E, Link H, Cytokine dichotomy in peripheral nervous system influences the outcome of experimental allergic neuritis: dynamics of MRNA expression for IL-1 beta, IL-6, IL-10, IL-12, TNF-alpha, TNF-beta, and cytolysin, Clin Immunol Inimunopathol 1997; 84: 85-94). TNF-alpha may also induce an increase in vascular permeability (Redford E J, Hall S M, Smith K J, Vascular chances and demyclination induced by the intra neural injection of tumour necrosis factor, Brain 1995; 118: 869-78; Wagner R, Myers R R, Endoneurial injection of TNF-alpha produces neuropathic pain behaviours, Neuroreport 1996; 7: 2897-901) and initiate coagulation (Jurd K M, Stephens C J, Black M M, Hunt B J, Endothelial cell activation in cutaneous vasculitis, Clin Exp Dermatol 1996; 21: 28-32; Nawroth P, Handley D, Matsueda G, De Waal R, Gerlach H, Blohm D, Stem D, Tumor necrosis factor/cachectin-induced intra vascular fibrin formation in meth A fibrosarcomas, J Exp Med 1988; 168: 637-47; van der Poll T, Jansen P M, Van Zee K J, Welborn M Br, de Jong I, Hack C E, Loetscher H, Lesslauer W, Lowry S F, Moidawer L L, Tumor necrosis factor-alpha induces activation of coagulation and fibrinolysis in baboons through an exclusive effect on the p55 receptor, Blood 1996; 88: 922-7). Further, TNF-alpha may be blocked by steroids (Baumgartner R A, Deramo V A, Beaven M A, Constitutive and inducible mechanisms for synthesis and release of cytokines in immune cell lines, J Immunol 1996; 157: 4087-93; Brattsand R, Linden M, Cytokine modulation by glucocorticoids: mechanisms and actions in cellular studies, Aliment Pharmacol Ther 1996; 10: 81-90; Iwamoto S, Takeda K, Possible cytotoxic mechanisms of TNF in vitro, Hum Cell 1990; 3: 107-12; Teoh K H, Bradley C A, Galt J, Burrows H, Steroid inhibition of cytokine-mediated vasodilation after warm heart surgery, Circulation 1995; 92: 11347-53; Wershil B K, Furuta G T, Lavigne J A, Choudhury A R, Wang Z S, Galli S J, Dexamethasone cyclosporin A suppress mast cell-leukocyte cytokine cascades by multiple mechanisms, Int Arch Allergy Immunol 1995; 107: 323-4.), and cyclosporin A (Dawson J, Hurtenbach U, MacKenzie A, Cyclosporin A inhibits the in vivo production of interleukin-Ibeta and tumour necrosis factor alpha, but not interleukin-6, by a T-cell independent mechanism, Cytokine 1996; 8: 882-8; Smith C S, Ortega G, Parker L, Shearer W T, Cyclosporin A blocks induction of tumor necrosis factor-alpha in human B lymphocytes, Biochem Biophys Res Commun 1994; 204: 383-90; Wasaki S, Sakaida I, Uchida K, Kiinura T, Kayano K, Oldta K, Preventive effect of cyclosporin A on experimentally induced acute liver injury in rats, Liver 1997; 17: 107-14; Wershil B K, Furuta G T, Lavigne J A, Choudhury A R, Wang Z S, Galli S J, Dexamethasone cyclosporin A suppress mast cell-leukocyte cytokine cascades by multiple mechanisms, Int Arch Allergy Immunol 1995; 107: 323-4). However, the blocking effect on TNF-alpha is not so pronounced by NSAID (Garcia-Vicuna R, Diaz-Gonzalez F, Gonzalez-Alvaro 1, del Pozo Ma, Mollinedo F, Cabanas C, Gonzalez-Amaro R, Sanchez-Madrid F, Prevention of cytokine-induced changes in leucocyte adhesion receptors by nonsteroidal antiinflammatory drugs from the oxicam family, Arthritis Rheum 1997; 40: 143-53; Gonzalez E, de la Cruz C, de Nicolas R, Egido J, Herrero-Beaumont G, Long-term effect of nonsteroidal anti-inflammatory drugs on the production of cytokines and other inflammatory mediators by blood cells of patients with osteosis, Agents Actions 1994; 41: 171-8; Herman J H, Sowder W G, Hess E V, Nonsteroidal antiinflammatory drug modulation of prosthesis pseudomembrane induced bone resorption, J Rheunutol 1994; 21: 338-43) and very low or the agonized by lidocaine (Bidani A, Heming T A, Effects of lidocaine on cytosolic pH regulation and stimulus-induced effector functions in alveolar macrophages, Lung 1997; 175: 349-61; Matsumori A, Ono K, Nishio R, Nose Y, Sasayaina S, Amiodarone inhibits production of tumor necrosis factor-alpha by human mononuclear cells: a possible mechanism for its effect in heart failure, Circulation 1997; 96: 1386-9; Pichler W J, Zanni M, von Greyerz S, Schnyder B, Mauri-Hellweg D, Wendland, T, High IL-5 production by human drug-specific T cell clones, Int Arch Allergy Immunol 1997; 113: 177-80; Takao Y, Mikawa K, Nishina Y, Maekawa N, Obara H, Lidocaine attenuates hyperoxic lung injury in rabbits, Acta Anaesthesiol Scand 1996; 40: 318-25).

It was recently observed that local application of nucleus pulposus may induce pain-related behavior in rats, particularly thermal hyperalgesia (Kawakami M, Tamaki T, Weinstein J N, Hashizume H, Nishi H, Meller S T, Pathomechanism of pain-related behaviour produced by allografts of intervertebral disc in the rat, Spine 1996; 21: 2101-7; Olmarker K, Myers R R, Pathogenesis of sciatic pain: Role of herniated nucleus pulposus and deformation of spinal nerve root and DRG, Pain, 1998, 78: 9-105). TNF-alpha has also been found to be related to such pain-behavioristic changes (DeLeo J A, Colbum R W, Rickman A J, Cytokine and growth factor immunohistochemical spinal profiles in two animal models of mononeuropathy, Brain Res 1997; 759: 50-7, Oka T, Wakugawa Y, Hosoi M, Oka K, Hari T, Intracerebroventricular injection of tumor necrosis factor-alpha induces thermal hyperalgesia in rats, Neuroimmunomodulation 1996; 3: 135-40; Sommer C, Schmidt C, George A, Toyka K V, A metalloprotease-inhibitor reduces pain associated behaviour in mice with experimental neuropathy, Neurosci Lett 1997; 237:45-8; Wagner R, Myers R R, Endoneurial injection of TNF-alpha produces neuropathic pain behaviours, Neuroreport 1996; 7: 2897-901), and also to neuropathies in general (Lin X H, Kashima Y, Khan M, Heller K B, Gu X Z, Sadun A A, An immunohistochemical study of TNF-alpha in optic nerves from AIDS patients, Curr Eye Res 1997; 16: 1064-8; Sharief M K, Ingram D A, Swash M, Circulating tumor necrosis factor-alpha correlates with electrodiagnostic abnormalities in Guillain-Barre syndrome, Ann Neurol 1997; 42: 6873; Sommer C, Schmidt C, George A, Toyka K V, A metalloprotease-inhibitor reduces pain associated behaviour in mice with experimental neuropathy, Neurosci Lett 1997; 237:45-8; Sorkin L S, Xiao W H, Wagner R, Myers R R, Tumour necrosis factor-alpha induces ectopic activity in nociceptive primary afferent fibres, Neuroscience 1997; 81: 255-62). However there are no studies that have assessed the possible presence of TNF-alpha in the cells of the nucleus pulposus.

To assess if TNF-alpha could be related to the observed nucleus pulposus induced reduction in nerve root conduction velocity it was necessary first to analyze if there was TNF-alpha in the nucleus pulposus-cells. The data clearly demonstrated that TNF-alpha was present in these cells. TNF-alpha is produced as a precursor (pro-TNF) that is bound to the membrane, and it is activated by cleavage from the cell-membrane by a zinc-dependent metallo-endopeptidase (i.e., TNF-alpha converting enzyme, TACE) (Black R A, Rauch C T, Kozlosky C J, Peschon I J, Slack J L, Wolfson M F, Castner B J, Stocking K L, Reddy P, Srinivasan S, Nelson N, Boiani N, Schooley K A, Gerhart M, Davis R, Fitzner J N, Johnson R S, Paxton R J, March C J, Cerretti D P, A metalloproteinase disintegrin that releases tumour-necrosis factor-alpha from cells, Nature 1997; 385: 729-33; Gearing A J, Beckett P, Christodoulou M, Churchill M, Clements J, Davidson A H, Drummond A H, Galloway W A, Gilbert R, Gordon J L, et al., Processing of tumour necrosis factor-alpha precursor by metalloproteinases, Nature 1994; 370: 555-7; Gazelle E J, Banda M J, Leppert D, Matrix metallo-proteinases in immunity, J Immunol 1996; 156: 14; Robache-Gallea S, Bruneau J M, Robbe H, Morand V, Capdevila C, Bhatnagar N, Chouaib S, Roman-Roman S, Partial purification and characterization of a tumor necrosis factor-alpha converting activity, Eur J Immunol 1997; 27: 1275-82; Rosendahl M S, Ko S C, Long D L, Brewer M T, Rosenzweig D, Hedl E, Anderson L, Pyle S M, Moreland J, Meyers M A, Kohno T, Lyons D, Lichenstein H S, Identification and characterization of a pro-tumor necrosis factor-alpha-processing enzyme from the ADAM family of zinc metalloproteases, J Biol Chem 1997; 272: 24588-93). This may thus relate well to experimental findings, where application of only the cell-membranes of autologous nucleus pulposus-cells induced nerve conduction velocity reduction, which indicated that the effects were mediated by a membrane-bound substance. Second, the effects of the TNF-alpha had to be blocked in a controlled manner. We then first chose to add the same selective antibody that was used for immunohistochemistry in series 1, which is known to also block the effects of TNF-alpha, to the nucleus pulposus before application. Also, we chose to treat the pigs with doxycycline, which is known to block TNF-alpha (Kloppenburg M, B-an B M, de Rooij-Dijk H H, Mitenburg A M, Daha M R, Breedveld F C, Dijkmans B A, Verweij C, The tetracycline derivative minocycline differentially affects cytokine production by monocytes and T lymphocytes, Antimicrob Agents Chemother 1996; 40: 934-40; Kloppenburg M, Verweij C L, Miltenburg A M, Verhoeven A J, Daha M R, Dikmans B A, Breeveld F C, The influence of tetracyclines on T cell activation, Clin Exp. Immunol 1995; 102: 635-41; Milano S, Arcoleo F, D'Agostino P, Cillari E, Intraperitoneal injection of tetracyclines protects mice from lethal endotoxemia downregulating inducible nitric oxide synthase in various organs and cytokine and nitrate secretion in blood, Antimicrob Agents Chemother 1997; 41: 117-21; Shapira L, Houri Y, Barak V, Halabi A, Soskoine W A, Stabholz A, Human monocyte response to cementum extracts from periodontally diseased teeth: effect of conditioning with tetracycline, J Periodontol 1996; 67: 682-7; Shapira L, Houri Y, Barak V, Soskolne W A, Halabi A, Stabholz A, Tetracycline inhibits *Porphyromonas gingivalis* lipopolysaccharide-induced lesions in vivo and TNF processing in vitro, J Periodontal Res 1997; 32: 183-8). However, due to the low pH of the doxycycline preparation, it was chosen to treat the pigs by intravenous injection instead of local addition to the nucleus pulposus since nucleus pulposus at a low pH has been found to potentiate the effects of the nucleus pulposus (Olmarker K, Byrod G, Comefjord M, Nordborg C, Rydevik B, Effects of methylprednisolone on nucleus pulposus-induced nerve root injury, Spine 1994; 19:1803-8; Iwabuchi M, Rydevik B, Kikuchi S, Olmarker K, Methylprednisolone reduces the early vascular permeability increase in spinal nerves by epidural nucleus pulposus application, Accepted for publication in Spine).

Two recently developed drugs for specific TNF-alpha inhibition were also included in the study. Infliximab is a chimeric monoclonal antibody composed of human constant and murine variable regions. Infliximab binds specifically to human TNF-alpha. As opposed to the monoclonal antibody used in series-2 for the 3-day observation period, infliximab was not administered locally in the autotransplanted nucleus pulposus, but instead was administered systemically in a clinically recommended dose (4 mg/kg).

Etanercept is a dimeric fusion protein consisting of the Fc portion of human IgG. The drug, etanercept, was administered in a dosage comparable to the recommended dose for pediatric use (0.5 mg/kg, twice a week).

The data regarding nerve conduction velocity showed that the reduction was completely blocked by the systemic-treatment and that the nerve conduction velocities in these series were close to the conduction velocity after application of a control substance (retro peritoneal fat) from a previous study (Olmarker K, Rydevik B, Nordborg C, Autologous nucleus pulposus induces neurophysiologic and histologic changes in porcine cauda equina nerve roots, Spine 1993; 18: 1425-32). Application of the anti-TNF-alpha-antibody to the nucleus pulposus also partially prevented the reduction in nerve conduction velocity. However, the reduction was not as pronounced as that observed for doxycycline, and the velocity in this series was not statistically different to the velocity in the series with untreated animals, given the wide deviation of the data.

The local anti-TNF-alpha antibody treatment only partially blocked the nucleus pulposus-induced reduction of nerve conduction velocity and the high standard deviation of the data could probably have at least three different explanations. First, if looking at the specific data within this group, it was found that the nerve conduction velocity was low in 2 animals (mean 37.5 m/s) and high in 3 animals (mean 81.3 m/s). There are thus 2 groups of distinctly different data within the anti-TNF-alpha treatment series. This will account for the high standard deviation and might imply that the blocking effect was sufficient in 3 animals and insufficient in 2 animals. The lack of effects in these animals could be based simply on the amount of antibodies in relation to TNF-alpha molecules not being sufficient, and if a higher dose of the antibody had been used, the TNF-alpha effects would thus have been blocked even in these animals. Such a scenario could then theoretically imply that TNF-alpha alone is responsible for the observed nucleus pulposus-induced effects, and that this could not be verified experimentally due to the amount of antibody being too low.

TNF-alpha may have various pathophysiologic effects. It may have direct effects on tissues such as nerve tissue and blood vessels, it may trigger other cells to produce other pathogenic substances and it may trigger release of more TNF-alpha both by inflammatory cells and also by Schwann-cells locally in the nerve tissue (Wagner R, Myers R R, Schwann cells produce tumor necrosis factor alpha: expression in injured non-injured nerves, Neuroscience 1996; 73: 625-9). There is thus reason to believe that even low amounts of TNF-alpha may be sufficient to initiate these processes and that there is a local recruitment of cytokine producing cells and a subsequent increase in production and release of other cytokines as well as TNF-alpha. TNF-alpha may therefore act as the "ignition key" of the pathophysiologic processes and play an important role for the initiation of the pathophysiologic cascade behind the nucleus pulposus-induced nerve injury. However, the major contribution of TNF-alpha may be derived from recruited, aggregated and maybe even extravasated leukocytes, and that successful pharmacologic block may be achieved only by systemic treatment.

In conclusion, for the first time a specific substance (TNF-alpha) has been linked to the nucleus pulposus-induced nerve root injury. This new information may be of significant importance for the continued understanding of nucleus pulposus-induced nerve injury as well as raising the question of the potential future clinical use of pharmacological interference with TNF-alpha and related substances, for treatment of sciatica.

The presence of TNF-alpha in pig nucleus pulposus-cells was thus immunohistochemically verified. Block of TNF-alpha by a locally applied monoclonal antibody limited the nucleus pulposus-induced reduction of nerve root conduction velocity, whereas intravenous treatment with doxycycline, infliximab, and etanercept significantly blocked this reduction. These data for the first time links one specific substance, TNF-alpha, to the nucleus pulposus-induced nerve injury.

Example 3

CDP-571 (HUMICADE®)

A 43-year old man with radiating pain corresponding to the left 4th lumbar nerve root is diagnosed as having sciatica with nerve root disturbance. He will be treated with 10 mg/kg of CDP-571 (HUMICADE®) intravenously in a single dose.

Example 4

D2E7

A 38-year old female with radiating pain and slight nerve dysfunction corresponding to the 1st sacral nerve on the left side is diagnosed as having a disc herniation with sciatica. She will be treated with an intravenous injection of 5 mg/kg of D2E7.

Example 5

CDP-870

A 41-year old female with dermatomal pain corresponding to the first sacral nerve root on the left side is examined revealing no neurological deficit but a positive straight leg raising test on the left side. She will be treated with an intravenous injection of 5 mg/kg of CDP-870.

Example 6

Combination treatment with a TNF inhibitor and an IL-1 inhibitor

Fourteen pigs, (body weight 25-30 kg) received an intramuscular injection of 20 mg/kg body weight of KETALAR® (ketamine 50 mg/ml, Parke-Davis, Morris Plains, N.J.) and an intravenous injection of 4 mg/kg body weight of HYPN-ODIL® (methomidate chloride 50 mg/ml, AB Leo, Helsingborg, Sweden) and 0.1 mg/kg body weight of STRESNIL® (azaperon 2 mg/ml, Janssen Pharmaceutica, Beerse, Belgium). Anesthesia was maintained by additional intravenous injections of 2 mg/kg body weight of HYPNODIL® and 0.05 mg/kg body weight of STRESNIL®. The pigs also received an intravenous injection of 0.1 mg/kg of STESOLID NOVUM® (Diazepam, Dumex, Helsingborg) after surgery.

Nucleus pulposus was harvested from the 5th lumbar disc through a retroperitoneal approach. Approximately 40 mg of the nucleus pulposus was applied to the sacrococcygeal cauda equina through a midline incision and laminectomy of the first coccygeal vertebra. In 5 pigs, the nucleus pulposus was mixed with 100 .mu.g of an anti-TNF-alpha antibody (anti-pig TNF-alpha monoclonal purified antibody, Endogen, Woburn, Mass., USA, Ordering Code MP-390) before application. In five pigs, the nucleus pulposus was mixed with both 100 .mu.g of an anti-TNF-alpha antibody and 100.mu.g of an anti-IL-1.beta. antibody (anti-pig IL-1.beta. monoclonal purified antibody, Endogen, Woburn, Mass., USA, Catalog No. MP-425). In the remaining 4 pigs, 2 mg of doxycycline (DOXYFERM®, doxycycline 20 mg/ml, Nordic, Malmo, Sweden) was mixed with the nucleus pulposus before application.

Three days after the application, the pigs were reanaesthetized by an intramuscular injection of 20 mg/kg body weight of KETALAR® and an intravenous injection of 35 mg/kg body weight of PENTOTHAL® (Thiopental sodium, Abbott lab, Chicago, Ill.). The pigs were ventilated on a respirator. Anesthesia was maintained by an intravenous bolus injection of 100 mg/kg body weight of Chloralose (alpha)-D(+)-glucochlor-alose, Merck, Darmstadt, Germany) and by a continuous supply of 30 mg/kg/hour of Chloralose. A laminectomy from the 4th sacral to the 3rd coccygeal vertebra was performed. The nerve roots were covered with SPONGOSTANE® (Ferrosan, Denmark). Local tissue temperature was continuously monitored and maintained at 37.5-38.0.degree. C. by means of a heating lamp.

The cauda equina was stimulated by two E2 subdermal platinum needle electrodes (Grass Instrument Co., Quincy, Mass.) which were connected to a Grass SD9 stimulator (Grass Instrument Co., Quincy, Mass.) and gently placed intermittently on the cauda equina first 10 mm cranial and then 10 mm caudal to the exposed area. To ensure that only impulses from exposed nerve fibers were registered, the nerve root that exited from the spinal canal between the two stimulation sites were cut. An EMG was registered by two subdermal platinum needle electrodes, which were placed into the paraspinal muscles in the tail approximately 10 mm apart. This procedure is reproducible and represents a functional measurement of the motor nerve fibers of the cauda equina nerve roots. The EMG was visualized using a Macintosh IIci computer provided with Superscope software and MacAdios II A/D converter (GW Instruments, Sommerville, Mass.). The separation distance between the first peaks of the EMG from the two recordings was determined and the separation distance between the two stimulation sites on the cauda equina was measured with calipers. The nerve conduction velocity between the two stimulation sites could thus be calculated from these two measurements.

The person performing the neurophysiologic analyzes was unaware of the experimental protocol for the individual animal, and after finishing the complete study the data were arranged in the three experimental groups and statistical differences between the groups were assessed by Student's t-test. For comparison, data from a previous study of the effects of application of retroperitoneal fat and autologous nucleus pulposus were included (Olmarker K, Rydevik B, Nordborg C, Autologous nucleus pulposus induces neurophysiologic and histologic changes in porcine cauda equina nerve roots, Spine 1993; 18(11): 1425-32).

The average nerve conduction velocity for the five groups is displayed in Table 3 below. According to the previous study, baseline nerve conduction velocity (fat) was 83 m/s and application of autologous nucleus pulposus induced a reduction of the conduction velocity to 45 m/s (Olmarker K, Rydevik B, Nordborg C, Autologous nucleus pulposus induces neurophysiologic and histologic changes in porcine cauda equina nerve roots, Spine 1993; 18(11): 1425-32). Application of doxycycline to the nucleus pulposus reduced the effects of the nucleus pulposus. Addition of an anti-TNF antibody was more efficient in reducing the nucleus pulposus effects than doxycycline. However, most efficient in blocking the nucleus pulposus induced reduction in nerve conduction velocity was the combined action of the anti-TNF and the anti-IL-1 antibody.

TABLE 3

| Nerve conduction velocity (m/s) 3 days after application | |
|---|---|
| Fat (n = 5) ) | 83 +/− 4 |
| NP + doxycycline (n = 4) | 53 +/− 22 |
| NP + anti-TNF (n = 5) | 64 +/− 28 |
| NP + anti-TNF and anti-IL-1-beta (n = 5) | 74 +/− 25 |
| NP (n = 5) | 45 +/− 16 |

Example 7

Combination treatment with a TNF inhibitor and an IL-1 inhibitor

Seven pigs, (body weight 25-30 kg) received an intramuscular injection of 20 mg/kg body weight of KETALAR-1® (ketamine 50 mg/ml, Parke-Davis, Morris Plains, N.J.) and an intravenous injection of 4 mg/kg body weight of HYPNODIL® (methomidate chloride 50 mg/ml, AB Leo, Helsingborg, Sweden) and 0.1 mg/kg body weight of STRESNIL® (azaperon 2 mg/ml, Janssen Pharmaceutica, Beerse, Belgium). Anesthesia was maintained by additional intravenous injections of 2 mg/kg body weight of HYPNODIL® and 0.05 mg/kg body weight of STRESNIL®. The pigs also received an intravenous injection of 0.1 mg/kg of STESOLID NOVUM® (Diazepam, Dumex, Helsingborg) after surgery.

Nucleus pulposus was harvested from the 5th lumbar disc through a retroperitoneal approach. Approximately 40 mg of the nucleus pulposus was applied to the sacrococcygeal cauda equina through a midline incision and laminectomy of the first coccygeal vertebra. In 2 pigs, the nucleus pulposus was mixed with 100 .mu.g of an anti-TNF-alpha antibody (anti-pig TNF-alpha monoclonal purified antibody, Endogen, Woburn, Mass., USA, Ordering Code MP-390) before application. In 2 pigs, the nucleus pulposus was mixed with 100 .mu.g of an anti-IL-1.beta. antibody (anti-pig IL-1.beta. monoclonal purified antibody, Endogen, Woburn, Mass., USA, Catalog No. MP-425). In five pigs, the nucleus pulposus was mixed with both 100 .mu.g of an anti-TNF-alpha antibody and 100 .mu.g of an anti-IL-1.beta. antibody.

Seven days after the application, the pigs were reanaesthetized by an intramuscular injection of 20 mg/kg body weight of KETALAR-1® and an intravenous injection of 35 mg/kg body weight of PENTOTHAL® (Thiopental sodium, Abbott lab, Chicago, Ill.). The pigs were ventilated on a respirator. Anesthesia was maintained by an intravenous bolus injection of 100 mg/kg body weight of Chloralose (alpha)-D(+)-glucochlor-alose, Merck, Darmstadt, Germany) and by a continuous supply of 30 mg/kg/hour of Chloralose. A laminectomy from the 4th sacral to the 3rd coccygeal vertebra was performed. The nerve roots were covered with SPONGOSTANE® (Ferrosan, Denmark). Local tissue temperature was continuously monitored and maintained at 37.5-38.0.degree. C. by means of a heating lamp.

The cauda equina was stimulated by two E2 subdermal platinum needle electrodes (Grass Instrument Co., Quincy, Mass.) which were connected to a Grass SD9 stimulator (Grass Instrument Co., Quincy, Mass.) and gently placed intermittently on the cauda equina first 10 mm cranial and then 10 mm caudal to the exposed area. To ensure that only impulses from exposed nerve fibers were registered, the nerve root that exited from the spinal canal between the two stimulation sites were cut. An EMG was registered by two subdermal platinum needle electrodes, which were placed into the paraspinal muscles in the tail approximately 10 mm apart. This procedure is reproducible and represents a functional measurement of the motor nerve fibers of the cauda equina nerve roots. The EMG was visualized using a Macintosh IIci computer provided with Superscope software and MacAdios II A/D converter (GW Instruments, Sommerville, Mass.). The separation distance between the first peaks of the EMG from the two recordings was determined and the separation distance between the two stimulation sites on the cauda equina was measured with calipers. The nerve conduction velocity between the two stimulation sites could thus be calculated from these two measurements.

The person performing the neurophysiologic analyzes was unaware of the experimental protocol for the individual animal, and after finishing the complete study the data were arranged in the three experimental groups and statistical differences between the groups were assessed by Student's t-test. The local animal research ethics committee approved the experimental protocol for this experiment. For comparison, data from a previous study of the effects of application of retroperitoneal fat and autologous nucleus pulposus were included (Olmarker K, Rydevik B, Nordborg C, Autologous nucleus pulposus induces neurophysiologic and histologic changes in porcine cauda equina nerve roots, Spine 1993; 18(11): 1425-32). The average nerve conduction velocity for the five groups is displayed in the Table 4 below. According to the previous study, baseline nerve conduction velocity (fat) was 76 m/s and application of autologous nucleus pulposus induced a reduction of the conduction velocity to 45 m/s (Olmarker K, Rydevik B, Nordborg C, Autologous nucleus pulposus induces neurophysiologic and histologic changes in porcine cauda equina nerve roots, Spine 1993; 18(11): 1425-32). Application of anti IL-1 showed a similar NCV as NP alone, indicating that the IL-1 had could not reduce the nucleus pulposus-induced reduction in nerve conduction velocity. Application of anti TNF limited the nucleus pulposus-induced reduction in nerve conduction velocity. Most efficient in reducing the nucleus pulposus-induced reduction in nerve conduction velocity was the combination of anti IL-1 and anti TNF. Since the effect in limiting the reduction in NCV was more than could be anticipated for addition of the effects of anti IL-1 and anti TNF, the data indicate a synergistic effect of the combination of the two cytokine antagonists.

TABLE 4

| Nerve conduction velocity (m/s) 7 days after application | |
|---|---|
| Fat (n = 5) ) | 76 +/− 11 |
| NP + anti-IL-1 beta (n = 2) | 46 +/− 11 |
| NP + anti-TNF (n = 2) | 59 +/− 6 |

TABLE 4-continued

| Nerve conduction velocity (m/s) 7 days after application | |
|---|---|
| NP + anti-TNF and anti-IL-1-beta (n = 3) | 78 +/− 2 |
| NP (n = 5) | 45 +/− 19 |

The amplitude of the obtained muscle action potentials (MAP's) grossly reflects the number of conducting axons. The amplitudes after application of the cytokine inhibitors were measured and compared to previous data of application of annulus fibrosus (NCV 75.+−.11 m/s) and nucleus pulposus at ph 6.0 (NCV 55.+−.22 m/s) from a previous study (Iwabuchi M, Rydevik B, Kikuchi S, Olmarker K, Effects of anulus fibrosus and experimentally degenerated nucleus pulposus on nerve root conduction velocity, Spine 2001; 26(15): 1651-5) and presented in table 5. Amplitudes of MAP seven days after application of cultured nucleus pulposus cells (NCV 52.+−.14 m/s) were also used as reference and example of the MAP amplitude in NP-exposed nerve roots (Kayama S, Olmarker K, Larsson K, Sjogren-Jansson E, Lindahl A, Cultured, autologous nucleus pulposus cells induce functional changes in spinal nerve roots, Spine 1998; 23(20): 2155-8). NP at pH 6.0 was obtained by slightly lowering the pH to 6.0 by addition of sodium lactate to form a 15 mmol/L lactate concentration and to adjusting the pH to 6.0 by adding a 2% HCl solution. The nerve recordings in the NP at pH 6.0 series were performed 3 days after application. The difference between application of NP at 6.0 and the combination of an anti-TNF and an anti-IL-1 inhibitor was statistically significant using Students t-test (p=0.0384), whereas the difference between NP at 6.0 and the two inhibitors alone were not. Similarly, the difference between application of NP cells and the combination of an anti-TNF and an anti-IL-1 inhibitor was statistically significant using Students t-test (p=0.0426), whereas the difference between NP cells and the two inhibitors alone were not. Since the effect in limiting the MAP amplitude was more than could be anticipated for addition of the effects of anti IL-1 and anti TNF, the data regarding MAP amplitude also indicate a synergistic effect of the combination of the two cytokine antagonists.

TABLE 5

| Muscle action potential amplitute (m/volts) | |
|---|---|
| Annulus fibrosus (n = 5) ) | 6.5 +/− 2.6 |
| NP + anti-IL-1 beta (n = 2) | 2.0 +/− 1.8 |
| NP + anti-TNF (n = 2) | 4.1 +/− 0.4 |
| NP + anti-TNF and anti-IL-1-beta (n = 3) | 6.1 +/− 2.6 |
| NP at pH 6.0 (n = 5) | 2.9 +/− 1.0 |
| NP cells (n = 5) | 2.8 +/− 1.2 |

The invention claimed is:

1. A method of treating or alleviating one or more symptoms of a nerve disorder mediated by nucleus pulposus in a mammal in need of such treatment comprising the step of administering a therapeutically effective amount of a TNF-α inhibitor to the mammal, wherein said TNF-α inhibitor is an antibody that blocks TNF-α activity.

2. The method of claim 1, wherein said antibody that blocks TNF-α activity is a complete or intact antibody.

3. The method of claim 1, further comprising administration of doxycycline.

4. The method of claim 1, wherein the TNT-α inhibitor is administered systemically.

5. The method of claim 1, wherein the TNF-α inhibitor is administered orally.

6. The method of claim 1, wherein the TNF-α inhibitor is administered intramuscularly.

7. The method of claim 1, wherein the TNF-α inhibitor is administered intravenously.

8. The method of claim 1, wherein said nerve disorder involves pain.

9. The method of claim 1, wherein said nerve disorder is a nerve root injury.

10. The method of claim 1, wherein said nerve disorder presents as sciatica.

11. The method of claim 1, wherein said nerve disorder is caused by a herniated disc.

12. The method of claim 1, wherein the antibody is administered locally.

13. The method of claim 1, wherein the antibody is administered epidurally to the mammal.

* * * * *

UNITED STATES PATENT AND TRADEMARK OFFICE
CERTIFICATE OF CORRECTION

PATENT NO.        : 7,708,995 B2
APPLICATION NO.   : 11/521093
DATED             : May 4, 2010
INVENTOR(S)       : Kjell Olmarker It is certified that error appears in the above-identified patent and that said Letters Patent is hereby corrected as shown below:

Column 1, line 4, please insert --CROSS-REFERENCE TO RELATED APPLICATIONS--;

Column 32, line 66 (Claim 4), please delete "TNT-α" and insert --TNF-α-- therefor.

Signed and Sealed this

Seventh Day of September, 2010

David J. Kappos
*Director of the United States Patent and Trademark Office*